US005585191A

United States Patent [19]
Gruber et al.

[11] Patent Number: 5,585,191
[45] Date of Patent: Dec. 17, 1996

[54] MELT-STABLE AMORPHOUS LACTIDE POLYMER FILM AND PROCESS FOR MANUFACTURE THEREOF

[75] Inventors: Patrick R. Gruber, St. Paul; Jeffrey J. Kolstad, Wayzata; Christopher M. Ryan, Dayton; Eric S. Hall, Crystal; Robin S. Eichen Conn, Minneapolis, all of Minn.

[73] Assignee: Cargill, Incorporated, Minneapolis, Minn.

[21] Appl. No.: 527,705

[22] Filed: Sep. 13, 1995

Related U.S. Application Data

[63] Continuation of Ser. No. 110,424, Aug. 23, 1993, Pat. No. 5,484,881, which is a continuation-in-part of Ser. No. 955,690, Oct. 2, 1992, Pat. No. 5,338,822.

[51] Int. Cl.⁶ .............................. B32B 27/36; B32B 9/04; C08G 63/08
[52] U.S. Cl. ....................... 428/480; 156/244.11; 264/75; 428/411.1; 525/413; 525/415; 528/354; 528/361
[58] Field of Search ................... 156/244.11; 264/75; 428/411.1, 480; 525/413, 415; 528/354, 361

[56] References Cited

U.S. PATENT DOCUMENTS

| | | | |
|---|---|---|---|
| 1,095,205 | 5/1914 | Gruter et al. | 528/361 |
| 1,849,107 | 3/1932 | Moss | 528/354 |
| 1,995,970 | 4/1935 | Dorough | 528/354 |
| 2,396,994 | 3/1946 | Filachione et al. | 528/354 |
| 2,703,316 | 3/1955 | Schneider | 528/354 |
| 2,758,987 | 8/1956 | Salzberg | 528/354 |
| 2,951,828 | 9/1960 | Zeile et al. | 528/354 |
| 3,268,487 | 8/1966 | Klootwijk | 528/357 |
| 3,322,791 | 5/1967 | Selman | 528/274 |
| 3,531,561 | 9/1970 | Trehu | 264/210 |

(List continued on next page.)

FOREIGN PATENT DOCUMENTS

| | | |
|---|---|---|
| 808731 | 3/1969 | Canada . |
| 863673 | 2/1971 | Canada . |
| 923245 | 3/1973 | Canada . |
| 0107591 | 2/1984 | European Pat. Off. . |
| 0299730 | 1/1989 | European Pat. Off. . |
| 0314245 | 5/1989 | European Pat. Off. . |
| 0052510 | 3/1992 | European Pat. Off. . |
| 0481732 | 4/1992 | European Pat. Off. . |
| 0507554 | 10/1992 | European Pat. Off. . |
| 0510998 | 10/1992 | European Pat. Off. . |
| 0515203 | 11/1992 | European Pat. Off. . |
| 0532154 | 3/1993 | European Pat. Off. . |
| 0533314 | 3/1993 | European Pat. Off. . |
| 267826 | 12/1913 | Germany . |
| 1083275 | 12/1960 | Germany . |
| 1543958 | 2/1970 | Germany . |

(List continued on next page.)

OTHER PUBLICATIONS

"Argus Product Data, Argus Dimyristyl Thiodipropionate", published on or before an unknown date in Aug., 1992, by Argus Division, Witco Corporation, 633 Court Street, Brooklyn, NY 11231–2193.

"Argus Product Data, Argus Disterayl Thiodipropionate", published on or before an unknown date in Aug., 1992, by Argus Division, Witco Corporation, 633 Court Street, Brooklyn, NY 11231–2193.

(List continued on next page.)

*Primary Examiner*—Shelley A. Dodson
*Attorney, Agent, or Firm*—Merchant, Gould, Smith, Edell, Welter & Schmidt, P.A.

[57] ABSTRACT

An amorphous film comprised of a lactide polymer. The lactide polymer comprises a plurality of poly(lactide) polymer chains, residual lactide in concentration of less than about 2 percent and water in concentration of less than about 2000 parts-per-million. A process for manufacturing an amorphous film with the lactide polymer composition is also disclosed.

28 Claims, 4 Drawing Sheets

U.S. PATENT DOCUMENTS

| | | | |
|---|---|---|---|
| 3,636,956 | 1/1972 | Schneider | 128/355.5 |
| 3,772,420 | 11/1973 | Glick et al. | 264/102 |
| 3,773,919 | 11/1973 | Boswell et al. | 424/19 |
| 3,839,297 | 10/1974 | Wassermann et al. | 528/357 |
| 3,887,699 | 6/1975 | Yolles | 424/19 |
| 3,912,692 | 10/1975 | Casey et al. | 528/354 |
| 4,045,418 | 8/1977 | Sinclair | 528/357 |
| 4,249,531 | 2/1981 | Heller et al. | 128/260 |
| 4,273,920 | 6/1981 | Nevin | 528/361 |
| 4,279,249 | 7/1981 | Vert et al. | 128/92 |
| 4,343,931 | 8/1982 | Barrows et al. | 528/291 |
| 4,441,496 | 4/1984 | Shalaby et al. | 28/354 |
| 4,529,792 | 7/1985 | Barrows et al. | 528/291 |
| 4,595,713 | 6/1986 | St. John | 523/105 |
| 4,643,734 | 2/1987 | Lin | 623/16 |
| 4,677,191 | 6/1987 | Tanaka et al. | 528/361 |
| 4,683,288 | 7/1987 | Tanaka et al. | 528/361 |
| 4,719,246 | 1/1988 | Murdoch et al. | 521/134 |
| 4,727,163 | 2/1988 | Bellis | 549/274 |
| 4,728,721 | 3/1988 | Yamamoto et al. | 528/361 |
| 4,766,182 | 8/1988 | Murdoch et al. | 525/413 |
| 4,789,726 | 12/1988 | Hutchinson | 528/354 |
| 4,797,468 | 1/1989 | DeVries | 528/254 |
| 4,800,219 | 1/1989 | Murdoch et al. | 525/413 |
| 4,835,293 | 5/1989 | Bhatia | 549/274 |
| 4,902,515 | 2/1990 | Loomis et al. | 424/486 |
| 4,950,258 | 8/1990 | Kawai et al. | 604/281 |
| 4,960,866 | 10/1990 | Bendix et al. | 528/499 |
| 4,981,696 | 1/1991 | Loomis et al. | 424/486 |
| 4,983,745 | 1/1991 | Muller et al. | 549/274 |
| 4,990,222 | 2/1991 | Aigner et al. | 203/91 |
| 5,011,946 | 4/1991 | Hess et al. | 549/274 |
| 5,023,349 | 6/1991 | Bhatia | 549/274 |
| 5,023,350 | 6/1991 | Bhatia | 549/274 |
| 5,041,529 | 8/1991 | Shinoda et al. | 528/354 |
| 5,043,458 | 8/1991 | Bhatia | 549/274 |
| 5,052,485 | 10/1991 | Nieuwenhuis et al. | 166/178 |
| 5,053,485 | 10/1991 | Nieuwenhuis et al. | 528/354 |
| 5,053,522 | 10/1991 | Muller | 549/274 |
| 5,076,983 | 12/1991 | Loomis et al. | 264/101 |
| 5,097,005 | 3/1992 | Tietz | 528/272 |
| 5,108,399 | 4/1992 | Eitenmuller et al. | 606/77 |
| 5,132,397 | 7/1992 | DeGuia | 528/354 |
| 5,134,171 | 7/1992 | Hammel et al. | 521/98 |
| 5,136,017 | 8/1992 | Kharas et al. | 528/354 |
| 5,142,023 | 8/1992 | Gruber et al. | 528/354 |
| 5,149,833 | 9/1992 | Hess et al. | 549/274 |
| 5,180,765 | 1/1993 | Sinclair | 524/306 |
| 5,225,490 | 7/1993 | Tokiwa et al. | 525/176 |
| 5,233,546 | 6/1993 | Morita et al. | 521/52 |
| 5,296,229 | 3/1994 | Grandjean | 424/444 |
| 5,338,822 | 8/1994 | Gruber et al. | 528/354 |
| 5,340,646 | 8/1994 | Morita et al. | 428/307.3 |

FOREIGN PATENT DOCUMENTS

| | | |
|---|---|---|
| 3632103 | 3/1988 | Germany. |
| 4-283227 | of 1992 | Japan. |
| 1040168 | 8/1966 | United Kingdom. |
| 1108720 | 4/1968 | United Kingdom. |
| 1351409 | 5/1974 | United Kingdom. |
| 2145422 | 3/1985 | United Kingdom. |
| WO90/01521 | 2/1990 | WIPO. |
| WO90/02015 | 1/1991 | WIPO. |
| WO91/02015 | 2/1991 | WIPO. |
| WO91/06601 | 5/1991 | WIPO. |
| WO92/00292 | 1/1992 | WIPO. |
| WO92/04412 | 3/1992 | WIPO. |
| WO92/04410 | 3/1992 | WIPO. |
| WO92/04413 | 3/1992 | WIPO. |
| WO92/05311 | 4/1992 | WIPO. |
| WO92/05168 | 4/1992 | WIPO. |
| WO92/05167 | 4/1992 | WIPO. |
| WO92/15340 | 9/1992 | WIPO. |
| WO93/02075 | 2/1993 | WIPO. |

OTHER PUBLICATIONS

"Argus Product Data, Mark 2140 Pentaerythrityl Octylthiopropionate", published on or before an unknown date in Aug., 1992, by Argus Division, Witco Corporation, 633 Court Street, Brooklyn, NY 11231–2193.

"Argus Product Data, Seenox 412S Pentaerythritol Tetraka (B–Laurythiopropionate)", published on or before an unknown date in Aug., 1992, by Argus Division, Witco Corporation, 633 Court Street, Brooklyn, NY 11231–2193.

"Argus Thiochemical Product Data, Argus Dilauryl Thidipropionate", published on or before an unknown date in Aug., 1992, by Argus Division, Witco Corporation, 633, Court Street, Brooklyn, NY 11231–2193.

"Argus Thiochemical Product Data, Argus Thiodipropionate", published on or before an unknown date in Aug., 1992, by Argus Division, Witco Corporation, 633 Court Street, Brooklyn, NY 11231–2193.

"Biocompatible Composite Would Be Completely Absorbed in the Body", *Advanced Materials,* vol. 12, No. 15, Aug., 1990, p. 6.

"Ethanox 398 Antioxidant, The First Fluorophosphonite Antioxidant", (publshied on or before an unknown date in Oct., 1990, by Ethyl Corporation, 451 Florida Blvd., Baton Rouge, LA 70801).

"GE Specialty Chemicals Product Guide CA–4001E", published on an unknown date in 1989, by General Electric ompany, 5th and Avery Street, Parkersburg, WV 26102.

"Hydrolytic Stability/Corrosivity of Phosphite Costabilizers", *Technical Bulletin* 89–04, published on an unknown date in 1989, by Stars Laboratory, Additives Division, Ciga–Geigy Corporation, Ardsley, NY 10502.

"Irganox 1010", a product brochure published on or before an unknown date in Aug., 1992 by Ciba–Geigy Corporation, Three Skyline Drive, Hawthorne, NY 10532.

"Irganox 1076 Antioxidant and Thermal Stabilizer", published on an unknown date in 1986 by Ciba–Geigy Corporation, Three Skyline Drive, Hawthorne, NY 10532.

"Irganox B–Blends Antioxidants and Process Stabilizers for Polymers", published on an unknown date in Mar., 1990 by Ciba–Geigy Corporation, Three Skyline Drive, Hawthorne, NY 10532.

"Irganox MD 1024, Metal Deactivator/Antioxidant", published on an unknown date prior to Aug., 1992, by Ciba–Geigy Corporation, Three Skyline Drive, Hawthorne, NY 10532.

"Naugard 445, Specialty Chemicals", (a product brochure published on or before May 1, 1990, by Uniroyl Chemical Company Inc., Middlebury, CT 06749.

"Naugard XL–1 Speciality Chemicals", product brochure publihsed on an unknown date in Feb., 1992, by Uniroyal Chemical Co., Inc., Middlebury, CT 06749.

"Polylactides Exhibit Degradability", *TAPPI Journal,* Sep. 1991, p. 42.

"The Resomer Resorbable Polyesters", ( published on or before an unknown date in Feb., 1991 by Boehringer Ingelheim KG, D–6507 Ingelheim, W. Germany).

"Tinuvin 123 Hindered Aminoether Light Stabilizer for Coatings", published on an unknown date in 1989, by Ciba–Geigy Corporation, Three Skyline Drive, Hawthorne, NY 10532.

"tinuvin 622LD Low Dust, Hindered Amine Light Stabilizer for Polymers FDA–cleared for Polyolefins", published on an unknown date before Aug., 1992, by Ciba–Geigy Corporation, Three Skyline Drive, Hawthorne, NY 10532.

Anderson, L. C., "An Injectible Sustained Release Fertility Control System", *Contraception,* vol. 13, No. 3, 375–384 (1976).

Bonsignore, P. V. et al., "Poly(lactic Acid) Degradable Plastics, Coatings and Binders", 1992, TAPPI Proceedings (Nonwovens Conference); pp. 129–140.

Carothers, W. et al., "Studies of Polymerization and Ring Formation. X. The Reversible Polymerization of Six–Membered Cyclic Esters", *American Chemical Society Journal*, vol. 54, pp 761–772.

Chabot, F. et al., "Configurational Structures of Lactic Acid Stereocopolymers as Determined by $^{13}C(^{1}H)$N.M.R.)", 1983, *Polymer*, vol. 24, pp. 53–59.

Chawla, A. and Chang, T., "In–Vivo Degradation of Poly(lactic acid) of Different Molecular Weights", 1985, *Biomat. Med. Dev. Art. Org.*, vol. 13, pp. 153–162.

Deanne, D. and Hammond, E., "Coagulation of Milk for Cheese–Making by Ester Hydrolysis", 1960, *Journal of Dairy Science*, vol. 43, pp. 1421–1429.

Enlow, W., "Process Stabilization with Phosphite Antioxidants", lecture notes distrubuted at a seminar entitled: *Principles of Polymer Degradation and Stabilization* in Orlando, Florida, Oct. 28–30, 1991, sponsored by The Institute of Materiasl Science, State University of New York at New Paltz.

Filachione, E. et al., "Lactic Acid Derivatives as Plasticizers Esters of Polymeric Lactic Acid", 1951, *Bur. Agric. Ind. Chem.*, vol. 11, pp. 1–11.

Garozzo, D. et al., "Primary Thermal Decomposition Processes in Aliphatic Polyesters Investigated by Chemical Ionization Mass Spectrometry", 1986, *Macromolecules*, vol. 19, pp. 1643–1649.

Gilding, D. K. et al., "Biodegradable Polymers for Use in Surgery–Polyglycolic/Polactic Acid Homo and Copolymers: 1.", *Polymer*, vol. 2, 1459–1464 (1979).

Gilding, D. K., "Biodegradable Polymers", *Biocompatibility of Clinical Implant Materials*, D. F. Williams, ed., vol. 2, 209–232 (1981).

Gilding, D. K., "Degradation of Polymers: Mechnisms and Implications for Biomedical Applications", *Biocompatibility of Clinical Implant Materials*, D. F. Williams, Ed., vol. 1, 43–65 (1981).

Gupta, M. and Deshmukh, V., "Thermal Oxidative Degradation of Poly–lactic Acid; Part 1: Activation Energy of Thermal Degradation in Air", 1982, *Colloid & Polymer Science*, vol. 260, pp. 308–311.

Gupta, M. and Deshmukh, V., "Thermal Oxidative Degradation of Poly–lactic Acid; Part II: Moleluar Weight and Electronic Spectra During Isothermal Heating", 1982, *Colloid & Polymer Science*, vol. 260, pp. 514–517.

Jackanicz, T. M., "Polylactic Acid as a Biodegradable Carrier for Contraceptive Steriods", *Contraception*, vol. 8, No. 3, 227–234 (1973).

Jamshidi, K. et al., "Thermal Characterization of Polylactides", Feb. 1988, *Polymer*, vol. 29, pp. 2229–2234.

Klemchuk, P., "Introduction to Polymer Degradation", lecture notes distributed at a seminar entitled: *Principles of Polymer Degradation and Stabilization* in Orland, Florida, Oct. 28–30, 1991, sponsored by The Institute of Materiasl Science, State University of New York at New Paltz.

Kohn, F. et al., "The Ring–Opening Polymerization of D,L–Lactide in the Melt Initiated With Tetraphenyltin", 1984, *Journal of Applied Polymer Science*, vol. 29, pp. 4265–4277.

Kricheldorf, H. and Serra, A., "Polylactones 6. Influance of Various Metal Salts on the Optical Purity of Poly(L–lactide)", 1985, *Polymer Bulletin*, vol. 14, pp. 497–502.

Kricheldorf, H. et al., "Polymerization Mechanism of Metal Alkoxide Initiated Polymerization of Lactide and Various Lactones", Apr. 1988, *Makromol.*, vol. 21, pp. 286–293.

Kulkarni, et al., "Biodegradable Poly(lactic acid) Polymers", 1971, *J. Biomed. Mater. Res.*, vol. 5, pp. 169–181.

Leenslag, J. and Pennings, A., "Synthesis of high–molecular weight poly(L–lactide) initiated with tin 2–ethylhexanoate", Apr. 1987, *Makromol. Chem.*, vol. 188, pp. 1809–1814.

Luderwald, I., "Thermal Degradation of Polyesters in the Mass Spectrometer", 1979, *Dev. Polymer Degradation*, vol. 2, pp. 77–89.

Makino, et al., "Preparation and In Vitro Degradation Properties of Polylactide Microcapsules", 1985, *Chem. Pharm. Bull.*, vol. 33, pp. 1195–1201.

McNeill, I. and Leiper, H., "Degradation Studies of some Polyesters and Polycarbonates–1. Polylactide: General Features of the Degradation Under Programmed Heating Conditions", 1985, *Polymer Degradation and Stability*, vol. 11, pp. 267–285.

McNeill, I. and Leiper, H., "Degradation Studies of Some Polyesters and Polycarbonates–2. Polylactide: Degradation Under Isothermal Conditions, Thermal Degradation Mechanism and Photolysis of the Polymer", Aug. 1995, *Polymer Degradation and Stability*, vol. 11, pp. 309–326.

Miller, R. A. et al., "Degradation Rates of Resorbable Implants (Polylacatates and Polyglycolates): Rate Modification with Changes in Pla/Pga Copolymer Rations", *J. Biomed. Mater. Res.*, vol. 11 711–719 (1977).

Nakamura et al., "Surgical Application of Biodegradable Films Prepared from Lactide–εCaprolactone Copolymers", 1987, *Bio. Materials and Clinical Applications*, vol. 7, pp. 759–764.

Reed, A. M. and Gilding, D. K., "Biodegradable Polymers for Use in Surgery Polyglycolic/Polylactic Acid Homo and Copolymers: 2. In Vitro Degradation", *Polymer*, vol. 22, No. 4, 494–498 (1981).

Schindler, A. et al., "Biodegradable Polymers for Sustained Drug Delivery", 1977, *Contemporary Topics in Polymer Science*, vol. 2, pp. 251–287.

Schwope, A. D. et al., "Lactic/Glycolic Acid Polymers as Narcotic Antagonist Delivery Systems", *Life Sciences*, vol. 17, 1877–1886 (1975).

Strobel, J. D., "Biodegradable Polymers", paper presented at Medical Textiles and Biomedical Polymers and Materials Conference held at Clemson, S.C., U.S.A., Dec. 5–6, 1989, Stolle Research and Development Corp., PD 712–01, pp. 1–32 and Attachments A1–A21.

Thomas, R., "Degradation and Stabilization of Eingineering Polymers", lecture notes distributed at a seminar entitled: *Principles of Polymer Degradation and Stabilization* in Orlando, Florida, Oct. 28–30, 1991, sponsored by The Institute of Materiasl Science, State University of New York at New Paltz.

Thomas, Sir John Muerig, "Solid Acid Catalysts", Apr. 1992, *Scientific American*, pp. 112–118.

Van Hummel, G. and Harkema, S., "Sturcture of 3,6–Dimethyl–1,4–Dioxane–2,5–Dione[D–, D–{–Lactide]", 1982, *Acta. Crystallogr.*, vol. B38, pp. 1679–1681.

Vert, M. and Chabot, F., "Stereoregular Bioresorbable Polyesters for Orthopaedic Surgery", 1981, *Makromol. Chem.*, Supp. 5, pp. 30–41.

Vert, M., "Bioresorbable Polymers for Temporary Therapeutic Applications", Mar. 1989, *Die Angwandte Makromolekulare Chemie.*, vol. 166–167, pp. 155–168.

Wise, D. L. et al., "Sustained Release of an Antimalarial Drug Using A Copolymer of Glycolic/Lactic Acid", *Life Sciences*, vol. 19, 867–874 (1976).

MELT-STABLE AMORPHOUS LACTIDE POLYMER FILM AND PROCESS FOR MANUFACTURE THEREOF

The present application is a continuing application of U.S. patent application Ser. No. 08/110,424 filed Aug. 23, 1993, which is now U.S. Pat. No. 5,484,881. The parent application (Ser. No. 08/110,424) was a continuation-in-part of U.S. application Ser. No. 07/955,690 filed Oct. 2, 1992, which is now U.S. Pat. No. 5,338,822. U.S. application Ser. Nos. 08/110,424 and 955,690 are incorporated herein by reference.

BACKGROUND OF THE INVENTION

1. Field of the Invention

The present invention relates to a film comprising a melt-stable, biodegradable amorphous lactide polymer composition and a process for manufacturing the film from a melt-stable, biodegradable lactide polymer.

2. Description of the Prior Art

The need for polymeric biodegradable films is well established. Films manufactured from blown or cast processes are well known. Typically in a blown film process, a plastic melt passes through a die which extrudes the molten plastic into an annular shape. Typically, the extruded film is extruded in an upward fashion. As the film moves upward, air is blown into the film which expands the film into a tubular shape. The tube is generally closed at some distance above the die, with a pair of nip rolls.

In a cast film process, a sheet is typically extruded from a slit die. The sheet is thereafter pulled through a series of rollers which cool the extruded sheet and may also elongate the length and width of the sheet to a desired dimension and thickness.

The use of films is widespread and well known in the art. The heaviest use of films occurs in the packaging and disposable article industries. Films employed in the packaging industry include films used in food and non-food packaging, merchandise bags and trash bags. In the disposable article industry, the general uses of films occur in the construction of diapers and personal hygiene articles, including tapes.

In light of depleting landfill space and adequate disposal sites, there is a need for biodegradable films. Currently, films comprising polymers such as polyethylene, polypropylene, polyethylene terephthlate, nylon, polystyrene, polyvinyl chloride and polyvinylidene chloride are popular for their superior extrusion and film-making properties. However, these films are not biodegradable. Furthermore, these films are generally noncompostable, which is undesirable from an environmental point of view.

Films have been developed which are generally considered to be biodegradable. These are films which purportedly have adequate properties to permit them to breakdown when exposed to conditions which lead to composting. Examples of such arguably biodegradable films include those made from polycaprolactone, starch biopolymers and polyvinyl alcohol.

Although films extruded from these materials have been employed in film containing articles, many problems have been encountered with their use. Often the films are not completely biodegradable or compostable. Furthermore, some biodegradable films may also be unduly sensitive to water, either limiting the Use of the film or requiring some type of surface treatment to the film, often rendering the film nonbiodegradable. Others have inadequate heat resistance for wide spread use.

The use of lactic acid and lactide to manufacture a biodegradable polymer is known in the medical industry. As disclosed by Nieuwenhuis et al. (U.S. Pat. No. 5,053,485), such polymers have been used for making biodegradable sutures, clamps, bone plates and biologically active controlled release devices. Processes developed for the manufacture of polymers to be utilized in the medical industry have incorporated techniques which respond to the need for high purity and biocompatability in the final product. These processes were designed to produce small volumes of high dollar-value products, with less emphasis on manufacturing cost and yield.

In order to meet projected needs for biodegradable packaging materials, others have endeavored to optimize lactide polymer processing systems. Gruber et al. (U.S. Pat. No. 5,142,023) disclose a continuous process for the manufacture of lactide polymers with controlled optical purity from lactic acid having physical properties suitable for replacing present petrochemical-based polymers.

Generally, manufacturers of polymers utilizing processes such as those disclosed by Gruber et al. will convert raw material monomers into polymer beads, resins or other pelletized or powdered products. The polymer in this form may then be sold to end users who convert, i.e., extrude, blow-mold, cast films, blow films, thermoform, injection-mold or fiber-spin the polymer at elevated temperatures to form useful articles. The above processes are collectively referred to as melt-processing. Polymers produced by processes such as those disclosed by Gruber et al., which are to be sold commercially as beads, resins, powders or other non-finished solid forms are generally referred to collectively as polymer resins.

Prior to the present invention, it is believed that there has been no disclosure of a combination of composition control and melt stability requirements which will lead to the production of commercially viable lactide polymer film.

It is generally known that lactide polymers or poly(lactide) are unstable. The concept of instability has both negative and positive aspects. A positive aspect is the biodegradation or other forms of degradation which occur when lactide polymers or articles manufactured from lactide polymers are discarded or composted after completing their useful life. A negative aspect of such instability is the degradation of lactide polymers during processing at elevated temperatures as, for example, during melt-processing by end-user purchasers of polymer resins. Thus, the same properties that make lactide polymers desirable as replacements for non-degradable petrochemical polymers also create undesirable effects during processing which must be overcome.

Lactide polymer degradation at elevated temperature has been the subject of several studies, including: I. C. McNeill and H. A. Leiper, *Polymer Degradation and Stability*, vol. 11, pp. 267–285 (1985); I. C. McNeill and H. A. Leiper, *Polymer Degradation and Stability*, vol. 11, pp. 309–326 (1985); M. C. Gupta and V. G. Deshmukh, *Colloid & Polymer Science*, vol. 260, pp. 308–311 (1982); M. C. Gupta and V. G. Deshmukh, *Colloid & Polymer Science*, vol. 260, pp. 514–517 (1982); Ingo Luderwald, *Dev. Polymer Degradation*, vol. 2, pp. 77–98 (1979); Domenico Garozzo, Mario Giuffrida, and Giorgio Montaudo, *Macromolecules*, vol. 19, pp. 1643–1649 (1986); and, K. Jamshidi, S. H. Hyon and Y. Ikada, *Polymer*, vol. 29, pp. 2229–2234 (1988).

It is known that lactide polymers exhibit an equilibrium relationship with lactide as represented by the reaction below:

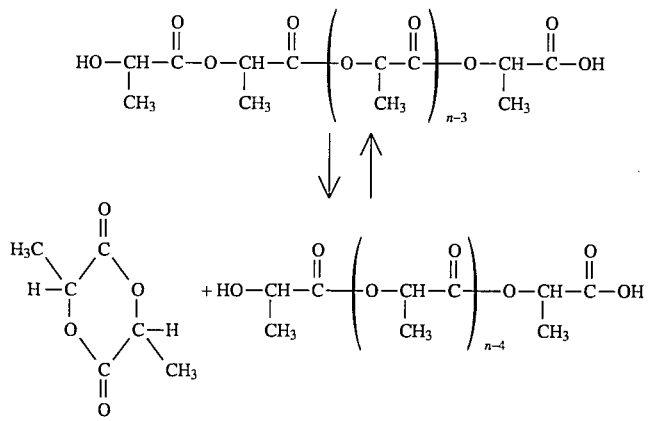

No consensus has been reached as to what the primary degradation pathways are at elevated processing temperatures. One of the proposed reaction pathways includes the reaction of a hydroxyl end group in a "back-biting" reaction to form lactide. This equilibrium reaction is illustrated above. Other proposed reaction pathways include: reaction of the hydroxyl end group in a "back-biting" reaction to form cyclic oligomers, chain scission through hydrolysis of the ester bonds, an intramolecular beta-elimination reaction producing a new acid end group and an unsaturated carbon-carbon bond, and radical chain decomposition reactions. Regardless of the mechanism or mechanisms involved, the fact that substantial degradation occurs at elevated temperatures, such as those used by melt-processors, creates an obstacle to use of lactide polymers as a replacement for petrochemical-based polymers. It is apparent that degradation of the polymer during melt-processing must be reduced to a commercially acceptable rate while the polymer maintains the qualities of biodegradation or compostability which make it so desirable. It is believed this problem has not been addressed prior to the developments disclosed herein.

As indicated above, poly(lactide)s have been produced in the past, but primarily for use in medical devices. These polymers exhibit biodegradability, but also a more stringent requirement of being bioresorbable or biocompatible. As disclosed by M. Vert, *Die Ingwandte Makromolekulare Chemie*, vol. 166–167, pp. 155–168 (1989), "The use of additives is precluded because they can leach out easily in body fluids and then be recognized as toxic, or, at least, they can be the source of fast aging with loss of the properties which motivated their use. Therefore, it is much more suitable to achieve property adjustment through chemical or physical structure factors, even if aging is still a problem." Thus, work aimed at the bioresorbable or biocompatible market focused on poly(lactide) and blends which did not include any additives.

Other disclosures in the medical area include Nieuwenhuis (European Patent No. 0 314 245), Nieuwenhuis (U.S. Pat. No. 5,053,485), Eitenmuller (U.S. Pat. No. 5,108,399), Shinoda (U.S. Pat. No. 5,041,529), Fouty (Canadian Patent No. 808,731), Fouty (Canadian Patent No. 923,245), Schneider (Canadian Patent No. 863,673), and Nakamura et al., *Bio. Materials and Clinical Applications*, Vol. 7, p. 759 (1987). As disclosed in these references, in the high value, low volume medical specialty market, poly(lactide) or lactide polymers and copolymers can be given the required physical properties by generating lactide of very high purity by means of such methods as solvent extraction or recrystallization followed by polymerization. The polymer generated from this high purity lactide is a very high molecular weight product which will retain its physical properties even if substantial degradation occurs and the molecular weight drops significantly during processing. Also, the polymer may be precipitated from a solvent in order to remove residual monomer and catalysts. Each of these treatments add stability to the polymer, but clearly at a high cost which would not be feasible for lactide polymer compositions which are to be used to replace inexpensive petrochemical-based polymers in the manufacture of films.

Furthermore, it is well-known that an increase in molecular weight generally results in an increase in a polymer's viscosity. A viscosity which is too high can prevent melt-processing of the polymer due to physical/mechanical limitations of the melt-processing equipment. Melt-processing of higher molecular weight polymers generally requires the use of increased temperatures to sufficiently reduce viscosity so that processing can proceed. However, there is an upper limit to temperatures used during processing. Increased temperatures increase degradation of the lactide polymer, as the previously-cited studies disclose.

Jamshidi et al., *Polymer*, vol. 29, pp. 2229–2234 (1988) disclose that the glass transition temperature of a lactide polymer, $T_g$, plateaus at about 57° C. for poly(lactide) having a number average molecular weight of greater than 10,000. It is also disclosed that the melting point, $T_m$, of poly (L-lactide) levels off at about 184° C. for semicrystalline lactide polymers having a number average molecular weight of about 70,000 or higher. This indicates that at a relatively low molecular weight, at least some physical properties of lactide polymers plateau and remain constant.

Sinclair et al. (U.S. Pat. No. 5,180,765) disclose the use of residual monomer, lactic acid or lactic acid oligomers to plasticize poly(lactide) polymers, with plasticizer levels of 2–60 percent. Loomis (U.S. Pat. No. 5,076,983) discloses a process for manufacturing a self-supporting film in which the oligomers of hydroxy acids are used as plasticizing agents. Loomis and Sinclair et al. disclose that the use of a plasticizer such as lactide or oligomers of lactic acid is beneficial to produce more flexible materials which are considered to be preferable. Sinclair et al., however, disclose that residual monomer can deposit out on rollers during processing. Loomis also recognizes that excessive levels of lactide or oligomers of lactic acid can cause unevenness in films and may separate and stick to and foul processing equipment. Thus, plasticizing as recommended, negatively impacts melt-processability in certain applications.

Accordingly, a need exists for a lactide polymer which is melt-stable under the elevated temperatures common to melt-processing resins in the manufacture of film. The needed melt-stable polymer composition must also exhibit sufficient compostability or degradability after its useful life as a film. Further, the melt-stable polymer must be processable in existing melt-processing equipment, by exhibiting sufficiently low viscosities at melt-processing temperatures while polymer degradation and lactide formation remains below a point of substantial degradation and does not cause excessive fouling of processing equipment. Furthermore, the lactide polymer must retain its molecular weight, viscosity and other physical properties within commercially-acceptable levels through the film manufacturing process. It will be further appreciated that a need also exists for a process for manufacturing such film. The present invention addresses these needs as well as other problems associated with existing lactide polymer compositions and manufacturing processes. The present invention also offers further advantages over the prior art, and solves other problems associated therewith.

SUMMARY OF THE INVENTION

According to the present invention, an amorphous biodegradable film is provided. The film comprises a melt-stable, lactide polymer composition comprising: a plurality of poly(lactide) polymer chains, the polymer being a reaction product of polymerizing a lactide mixture comprising more than about 1 percent by weight meso-lactide. The remaining lactide can be L-lactide, D-lactide or mixtures thereof. The polymer, because it is amorphous, exhibits a net melting endotherm of less than about 10 joules per gram of poly(lactide). The polymer has a residual lactide in a concentration of less than about 2 percent by weight and water in a concentration of less than about 2,000 parts per million. A process for the manufacture of the film is also provided. For the purposes of the present invention, the film may be manufactured from any number of methods and is not to be limited by the particular method.

Optionally, stabilizing agents in the form of anti-oxidants and water scavengers may be added. Further, plasticizers, nucleating agents, anti-static agents, slip aids and anti-blocking agents may be added. The resultant film is biodegradable and may be disposed of in an environmentally sound fashion.

The present invention recognizes conditions and compositions which affect the crystallization of poly(lactide) films. In particular, it is shown that in certain cases an amorphous film may become semicrystalline. Compositions which assure an amorphous, non-crystallizing film, are pointed out.

Poly(lactide) is a polymeric material which offers unique advantages as a film not only in the biodegradable sense, but in the manufacturing process as well.

The films of the present invention may be used in articles such as diapers, packaging film, shrink wrap film, agricultural mulch film, bags and tape.

The films of the present invention are superior in diaper constructions as compared to other films such as polypropylene or polyethylene. The typical construction of a diaper comprises an outer, water impervious back sheet, a middle absorbent layer and an inner layer. The outer back sheet, comprising the exterior of the diaper, is desirable from an environmental point of view if it is biodegradable. The film of the present invention satisfies this environmental concern by being biodegradable and compostable.

Furthermore, a poly(lactide) film, unlike other biodegradable polymers, is believed to not support microbial growth during storage and typical film use. Starch or other biodegradable polymers, when exposed to warm, damp environments, will promote the growth of unhealthy microbes. This is undesirable in personal hygiene products. Thus, the present invention has yet another advantage over prior biodegradable polymers.

Another advantage of the present invention is the high surface energy of poly(lactide) films. Poly(lactide) is a material with a relatively high surface energy, when compared to other films. As the surface energy of an extruded film increases, the driving-force to remain intact and to minimize surface area increases, therefore the tendency to form a smooth, coherent, high gloss film increases. A high surface energy film also has the advantage of having a surface which is easier to print on. This is an important feature in packaging applications and diapers.

The film of the present invention exhibits a higher surface energy than untreated polyolefin films. In order to produce a satisfactory printing surface, these films must first be modified. This not only increases the costs associated with production of the films, but the modification treatment will diffuse into the film and will produce an unsatisfactory printing surface.

The surface energy of substantially pure poly(lactide) films of the present invention is about 44 dynes/cm. This leads to a surface with satisfactory printing characteristics without surface modification. Slip aids or other additives may reduce the surface energy. Additionally, inks which are typically more difficult to apply onto paper coatings, like water based inks, may be applied directly to poly(lactide).

Poly(lactide) is a relatively low viscosity polymer which allows the extrusion of the film to be done at lower temperatures than traditional films. This results in a cost savings to the converter because the extrusion equipment will not require as much power when run at lower temperatures.

Heat sealability is also a property of films which is desirable. Poly(lactide) can be heat sealed at temperatures lower than 70° C., at line pressures lower than 40 psi, and at times less than 2 sec.

It has been found that to improve certain properties for poly(lactide), it may be advantageous to blend a second polymer with poly(lactide). The polymer chosen for blending with poly(lactide) will be one which has the properties necessary for the particular need and is compatible with poly(lactide) to the extent that the particular properties of poly(lactide) are improved. Incompatibility often results in a polymer blend which has inferior properties, such as very low tensile strength and modulus. Properties which may be increased include elongation, heat resistance, rheological properties, degradability, and barrier properties to oxygen, moisture, or carbon dioxide.

Polymer Blends

To improve certain properties of poly(lactide), it may be advantageous to blend a second polymer with poly(lactide). The polymer chosen for blending with poly(lactide) will be one which has the properties necessary for the particular need and is compatible with poly(lactide) to the extent that the particular properties of poly(lactide) are improved. Incompatibility often results in a polymer blend which has inferior properties, such as very low tensile strength, rheological properties, degradability, and barrier properties to oxygen, moisture or carbon dioxide. Polymers which may be useful for improving the film properties of poly(lactide) include aliphatic polyesters or polyamides made by both ring opening and condensation polymerization, esterified cellulose resins, derivitized starch, polyvinylacetate and any of its partially hydrolyzed products including polyvinylalcohol, polyethers including poly(ethylene oxide), polycarbonates, polyurethanes including those based on aliphatic isocyanates, polyanhydrides, natural rubber and its derivatives including epoxidized natural rubber, block copolymers of styrene and isoprene or butadiene and the hydrogenated version of those polymers, polyacrylates and methacrylates, polyolefins, and polystyrene.

Examples of particular interest include polymers which are also degradable including poly(caprolactone), poly(hydroxybutyrate hydroxyvalerate), cellulose acetate, cellulose acetate butyrate, cellulose acetate propionate, and poly(vinyl alcohol).

These polymers may be blended with poly(lactide) in percentages of about 1 to 95% by weight to make films of improved properties as shown in Example 1.

The above described features and advantages along with various other advantages and features of novelty are pointed out with particularity in the claims of the present application. However, for a better understanding of the invention, its advantages, and objects attained by its use, reference should be made to the drawings which form a further part of the present application and to the accompanying descriptive matter in which there is illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENT(S)

Figure 1:
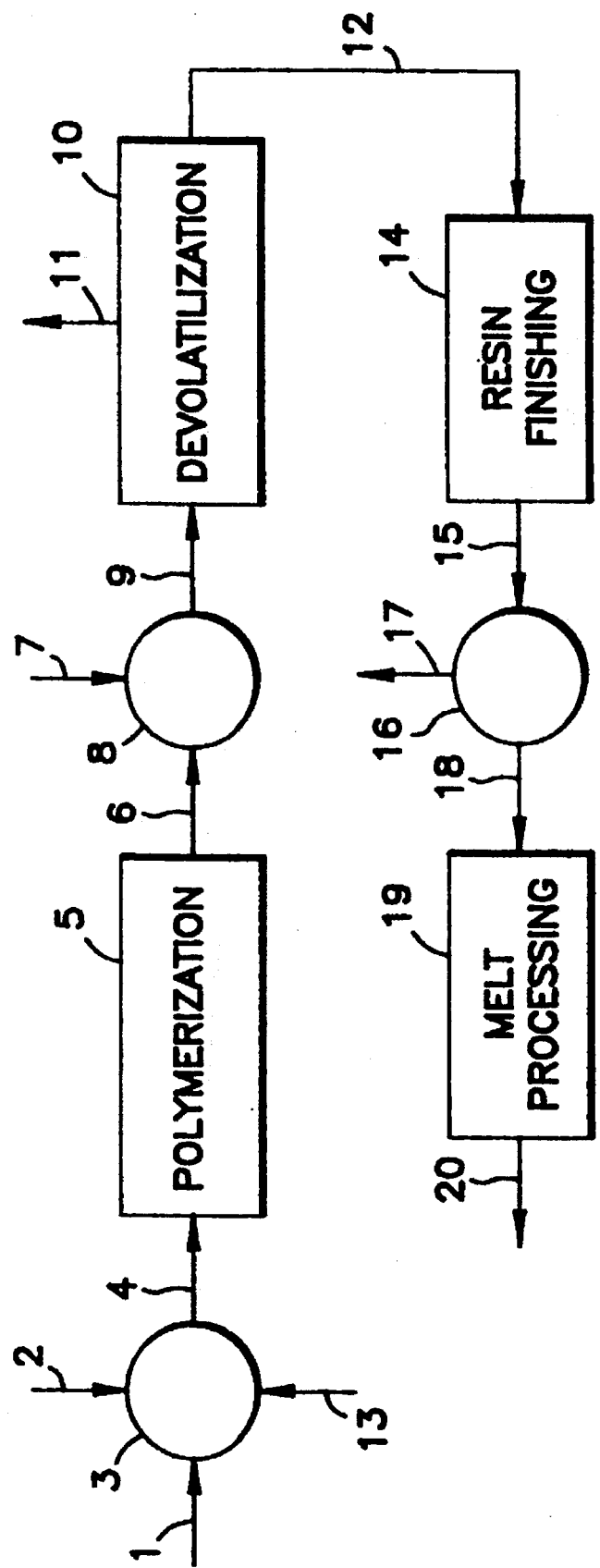
FIG. 1 is a schematic representation of a preferred process for the manufacture of a melt-stable lactide polymer composition.

The amorphous lactide polymer compositions used in films disclosed herein focus on meeting the requirements of the melt-processor of a lactide polymer resin such as that produced from a process disclosed by Gruber et al. However, the present invention is directed to a poly(lactide) film and is not limited to the lactide polymer composition or process of Gruber et al. Any lactide polymer composition, which comes within the scope of this invention, may be used as a film. As disclosed herein, the problems of degradation, fouling, and lactide formation during melt-processing of lactide polymers are addressed through suggested ranges of molecular weights and compositional limits on impurities such as residual monomer, water and catalyst along with the use of stabilizing agents and catalyst-deactivating agents.

In general, according to the present invention, a melt-stable, amorphous lactide polymer film and a process for manufacturing a melt-stable amorphous lactide polymer film from a melt-stable lactide polymer are disclosed. The use of the term "film" includes not only films, but sheets as well. There are no thickness limitations with the present invention, other than those present from processing limitations. Lactide polymers are useful due to their recycleable and biodegradable nature. Furthermore, lactide polymers are compostable as illustrated in Example 15 below. Applicants believe the hydrolysis of the ester may be the key to or the first step in degradation of a lactide polymer composition. The mechanism of degradation is not key to the films of the present invention, however it must be recognized that such degradation makes lactide polymers desirable as replacements for presently-utilized nondegradable petrochemical-based polymers used for films.

Applicants have found that the instability of lactide polymers which leads to the beneficial degradation discussed above also creates processing problems. These processing problems include generation of lactide monomer at elevated temperatures and loss in molecular weight believed due to chain scission degradation of the ester bonds and other depolymerization reactions which are not completely understood. No consensus has been reached as to what are the primary degradation pathways at elevated processing temperatures. As previously disclosed, these may include such pathways as equilibrium-driven depolymerization of lactide polymers to form lactide and chain scission through hydrolysis of the ester bonds along with other pathways. For purposes of the present invention, the exact mechanism of degradation at elevated temperatures is not critical.

It is to be understood, however, that degradation of lactide polymers is both beneficial and detrimental. Benefits derive from degradability when articles manufactured from such polymers are discarded. The same or similar types of degradation are detrimental if they occur during processing or prior to the end of the article's useful life.

Lactic acid has two optical isomers, L-lactic acid, also known as (S)-lactic acid, and D-lactic acid, also known as (R)-lactic acid. Three forms of lactide can be derived from the two forms of lactic acid. They are L,L-lactide, also known as L-lactide and which comprises two (S)-lactic acid residuals; D,D-lactide, also known as D-lactide and which comprises two (R)-lactic acid residuals; and meso-lactide, which comprises one each of (R)- and (S)-lactic acid residuals. A 50/50 solid mixture of D-lactide and L-lactide with a melting point of about 126° C. is sometimes called D,L-lactide. At temperatures higher than the melting point, it is essentially a liquid mixture of D-lactide and L-lactide.

The similarities and differences between poly(lactic acid) and various poly(lactide)s can best be examined by looking at the distribution of (R) and (S)-lactic acid residuals in the polymers. An L-lactide or D-lactide will introduce a pair of (S) or (R) residuals into the chain, respectively. Meso-lactide introduces an (R,S) or (S,R) dyad. The characteristics of the final polymer will depend for various applications, on the sequencing of the (R) and (S) residuals.

Crystallinity requires relatively long sequences of a particular residual, either long sequences of (R) or of (S). The length of the interrupting sequences may be important for establishing other features of the polymer, such as the rate at which it crystallizes, the melting point of the crystalline phase, or melt processability. The table below shows the expected statistical distribution of the major and minor sequence lengths assuming random polymerization and neglecting transesterification. The table shows data for mixtures containing predominately the (S) configuration, the same results would be obtained for mixtures containing predominately the (R) configuration.

| Monomer mix | Optical Composition | Probability major sequence having length at least n = | | | Probability minor sequence having length at least n = | | |
|---|---|---|---|---|---|---|---|
| | | 6 | 10 | 20 | 1 | 2 | 3 |
| Lactic Acid | | | | | | | |
| 95 L/5 D | 95 S/5 R | 0.77 | 0.63 | 0.38 | 1.0 | 0.05 | 0.002 |
| 90 L/10 D | 90 S/10 R | 0.59 | 0.39 | 0.14 | 1.0 | 0.10 | 0.01 |
| Lactide | | | | | | | |
| 95 L/5 D | 95 S/5 R | 0.90 | 0.81 | 0.63 | 1.0 | 1.0 | 0.05 |
| 90 L/10 D | 90 S/10 R | 0.81 | 0.66 | 0.39 | 1.0 | 1.0 | 0.10 |
| 85 L/15 D | 85 S/15 R | 0.72 | 0.52 | 0.23 | 1.0 | 1.0 | 0.15 |
| 80 L/20 D | 80 S/20 R | 0.64 | 0.41 | 0.13 | 1.0 | 1.0 | 0.20 |
| 95 L/5 meso | 97 S/3 R | 0.88 | 0.79 | 0.61 | 1.0 | 0.01 | 0.00 |
| 90 L/10 meso | 95 S/5 R | 0.77 | 0.62 | 0.37 | 1.0 | 0.02 | 0.00 |
| 85 L/15 meso | 92 S/8 R | 0.67 | 0.48 | 0.21 | 1.0 | 0.04 | 0.00 |
| 80 L/20 meso | 90 S/10 R | 0.57 | 0.37 | 0.12 | 1.0 | 0.05 | 0.00 |

The table above shows, that for the L-lactide system, D-lactide or meso-lactide result in similar major sequence lengths at similar levels. The major sequence length is believed to dominate whether or not crystallization can occur. Fischer et al. [Fischer, E. W., Sterzel, H. J., and Wegner, G., Kolloid-Z. u.Z Polymere 251, p980–990 (1973)] studied the system of L-lactide and D-lactide and reported that crystallization did not occur if the minor component was more than 15% of the polymerization mixture. Our results, documented in Example 24, show that polymers made of L-lactide and meso-lactide will not crystallize when the polymerization mixture contains more than about 15% of the meso-lactide. These results are consistent with the table above, and suggest that a lactide or lactic acid polymer is crystallizable provided that there is at least a 0.5 probability that sequences of the major conformation comprise at least 10 lactic acid residuals.

The table above also shows that polymers of predominately L-lactide with either D-lactide or meso-lactide as minor components have dramatically different sequences of the minor component. For polymers made of L-lactide and meso-lactide there is no chance of having three or more (R)-lactic acid residuals in a row, and a very low probability of having two in a row. For polymers made of L-lactide with low concentrations of D-lactide, the (R)-lactic acid residuals always appear in at least a sequence of length two, with a significant fraction appearing as sequences of length four.

Polymers made either from L- and D-lactic acid (by direct condensation, for example) or from L-lactide with small amounts of meso-lactide have a somewhat similar structure when compared at similar levels of (S) and (R) residuals, as shown in the table above.

Melt-Processing

It is believed that a manufacturer of lactide polymers from a lactide monomer will produce a lactide polymer resin which is in the form of beads or pellets. The melt-processor will convert the resin to a film by elevating the temperature of the resin above at least its glass transition temperature but normally higher and extruding the resin into a film. It is to be understood that the conditions of elevated temperature used in melt-processing cause degradation of lactide polymers during processing. Degradation under melt-processing conditions is shown experimentally in Example 7 based on equilibrium, Example 10 based on catalyst concentration, Example 11 based on catalyst activity, Example 13 based on use of stabilizers and Example 14 based on moisture content. As can be seen in these examples, it is understood that several factors appear to affect the rate of degradation during melt-processing. Applicants have addressed these factors in a combination of compositional requirements and the addition of stabilizing or catalyst-deactivating agents to result in a polymer of lactide which is melt-stable.

In addition, melt-processing frequently produces some proportion of trimmed or rejected material. Environmental concerns and economical efficiencies dictate that this material be reused, typically by regrinding and adding back the material into the polymer feed. This introduces additional thermal stress on the polymer and increases the need for a melt-stable polymer composition.

Melt Stability

The lactide polymers of the present invention are melt-stable. By "melt-stable" it is meant generally that the lactide polymer, when subjected to melt-processing techniques, adequately maintains its physical properties and does not generate by-products in sufficient quantity to foul or coat processing equipment. The melt-stable lactide polymer exhibits reduced degradation and/or reduced lactide formation relative to known lactide polymers. It is to be understood that degradation will occur during melt-processing. The compositional requirements and use of stabilizing agents as disclosed herein reduces the degree of such degradation to a point where physical properties are not significantly affected by melt-processing and fouling by impurities or degradation by-products such as lactide does not occur. Furthermore, the melt-stable polymer should be melt-processable in melt-processing equipment such as that available commercially. Further, the polymer will preferably retain adequate molecular weight and viscosity. The polymer should preferably have sufficiently low viscosity at the temperature of melt-processing so that the extrusion equipment may create an acceptable film. The temperature at which this viscosity is sufficiently low will preferably also be below a temperature at which substantial degradation occurs.

Polymer Composition

The melt-stable lactide polymer film of the present invention comprises a plurality of poly(lactide) polymer chains having a number average molecular weight from about 10,000 to about 300,000. In a preferred composition for a film, the number average molecular weight ranges from about 20,000 to about 275,000. In the most preferred composition, the number average molecular weight ranges from about 40,000 to about 250,000.

The molecular weight of a polymer sample can be determined through the use of gel permeation chromatography (GPC). In the present case, the GPC analysis was conducted with an Ultrastyragel® column from Waters Chromatography. The mobile phase was chloroform. A refractive index detector with molecular weight calibration using polystyrene standards was used. The GPC temperature was 35° C. Molecular weights were determined by integrating from the highest molecular weight fraction down to 4,000 amu. The region below 4,000 amu is excluded from the calculations of molecular weight in order to improve reproducibility of the number average molecular weight. This material may be separately reported as "oligomers" and residual lactide, as in Example 11.

As detailed in Example 9, it appears that the physical properties such as modulus, tensile strength, percentage elongation at break, impact strength, flexural modulus, and flexural strength remain statistically constant when the lactide polymer samples are above a threshold molecular weight. As detailed in Example 22, there is a practical upper limit on molecular weight based on increased viscosity with increased molecular weight. In order to melt-process a high molecular weight lactide polymer, the melt-processing temperature must be increased to reduce the viscosity of the polymer. As pointed out in the Examples, the exact upper limit on molecular weight must be determined for each melt-processing application in that required viscosities vary and residence time within the melt-processing equipment will also vary. Thus, the degree of degradation in each type of processing system will also vary. Based on the disclosure of Example 22, it is believed that one could determine the suitable molecular weight upper limit for meeting the viscosity and degradation requirements in any application.

In the present invention, the film comprising a melt-stable lactide polymer is substantially amorphous. In the present invention, a film is considered to be amorphous if it exhibits a net melting endotherm of less than about 10 J/gm of poly(lactide) when analyzed by a differential scanning calorimeter DSC. To determine whether a film is amorphous it can be tested in a differential scanning calorimeter (DSC), such as marketed by Mettler. An accurately weighed sample of the film, weighing between 5 mg and 15 mg, is placed in the test ampule. A suitable temperature program is to start at −20° C. and scan at 20° C./min to 200° C. Typical features which may be observed include a glass transition at a temperature designated Tg, a relaxation endotherm peak immediately following Tg, a crystallization exotherm peak (generally in the range of 70°–140° C.), and a melting endotherm peak (generally in the range of 100°–200° C.). In the present invention, a film is considered to be amorphous if it exhibits a net melting endotherm of less than about 10 J/gm of poly(lactide). The net melting endotherm is the energy of the melting endotherm less the energy of the crystallization exotherm, if present.

As detailed in Examples 26, 27 and 27, an amorphous polymer potentially may crystallize during a hydrolysis test, thereby losing its quality of being amorphous. This test is believed to represent a critical step in the composting of poly(lactide). As detailed in Example 15, amorphous polymers exhibit superior degradability when subjected to a compost test.

Figure 4:
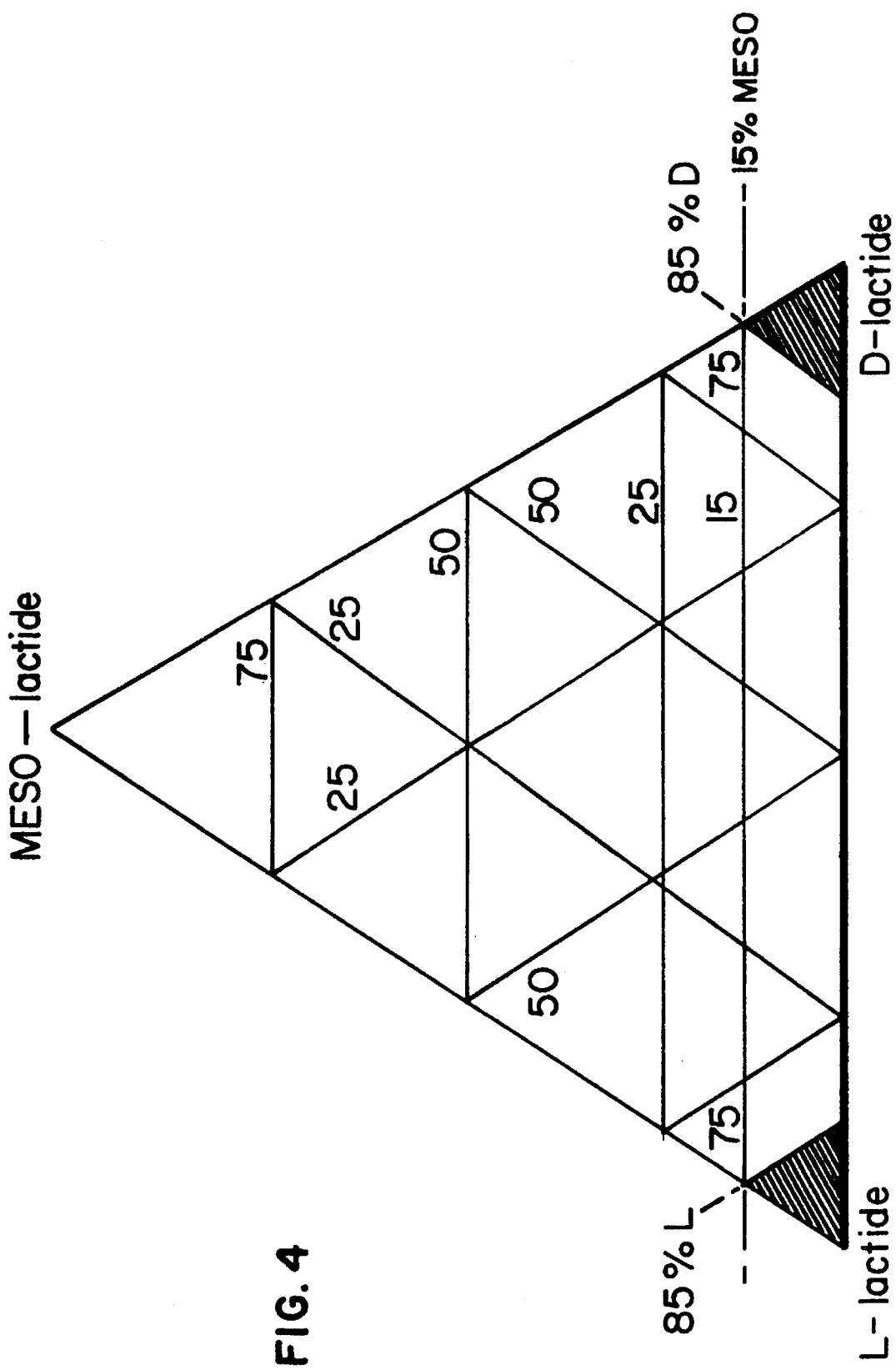
FIG. 4 is a phase diagram for meso-lactide, L-lactide and D-lactide.

In a preferred embodiment, the film is non-crystallizing, in addition to being amorphous. A non-crystallizing film is one which does not develop crystallinity when subjected to a proscribed annealing procedure, such as detailed in Example 24. As detailed in Example 24, a non-crystallizing polymer can be made from a lactide composition containing at least about 12 percent by weight of meso-lactide. FIG. 4 illustrates a preferred embodiment, showing a non-crystallizing polymer needing to have at least 15 percent by weight meso-lactide when the other component is either pure L-lactide or pure D-lactide. However, Example 24 illustrates the meso-lactide concentration can be as low as above 12 percent by weight and still be non-crystallized. If the remaining lactide is not substantially optically pure, then less meso-lactide would be required to prevent crystallization. Meso-lactide concentrations can be as low as 1% and still result in an amorphous polymer.

In addition to using the composition of the poly(lactide) to ensure non-crystallizing of the polymer, copolymers, blends or other structural modifications to the polymer could be used to prevent crystallization.

The residual monomer concentration in the melt-stable lactide polymer composition is less than about 2.0 percent by weight. In a preferred composition, the lactide concentration is less than about 1.0 percent by weight and a most preferred composition has less than about 0.5 percent by weight of lactide. Contrary to disclosures in the art, Applicants have found that the monomer cannot be used as a plasticizing agent in the resin of the present invention due to significant fouling of the extrusion equipment. As detailed in Example 16, it is believed the low levels of monomer concentration do not plasticize the final polymer.

The water concentration within the melt-stable lactide polymer composition is less than about 2,000 parts-per-million. Preferably this concentration is less than 500 parts-per-million and most preferably less than about 100 parts-per-million. As detailed in Example 14, the polymer melt-stability is significantly affected by moisture content. Thus, the melt-stable polymer of the present invention must have the water removed prior to melt-processing. Applicants recognize that water concentration may be reduced prior to processing the polymerized lactide to a resin. Thus, moisture control could be accomplished by packaging such resins in a manner which prevents moisture from contacting the already-dry resin. Alternatively, the moisture content may be reduced at the melt-processor's facility just prior to the melt-processing step in a dryer. Example 14 details the benefit of drying just prior to melt-processing and also details the problems encountered due to water uptake in a polymer resin if not stored in a manner in which moisture exposure is prevented or if not dried prior to melt-processing. As detailed in these examples, Applicants have found that the presence of water causes excessive loss of molecular weight which may affect the physical properties of the melt-processed polymer.

In a preferred composition of the present invention, a stabilizing agent is included in the polymer formulation to reduce degradation of the polymer during production, devolatilization, drying and melt processing by the end user. The stabilizing agents recognized as useful in the present films may include antioxidants and/or water scavengers. Preferred antioxidants are phosphite-containing compounds, hindered phenolic compounds or other phenolic compounds. The antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof. As detailed in Example 13, many commercially-available stabilizing agents have been tested and fall within the scope of the present melt-stable lactide polymer film. Biodegradable antioxidants are particularly preferred.

The water scavengers which may be utilized in preferred embodiments of the melt-stable lactide polymer film include: carbodiimides, anhydrides, acyl chlorides, isocyanates, alkoxy silanes, and desiccant materials such as clay, alumina, silica gel, zeolites, calcium chloride, calcium carbonate, sodium sulfate, bicarbonates or any other compound which ties up water. Preferably the water scavenger is degradable or compostable. Example 19 details the benefits of utilizing a water scavenger.

In a preferred composition of the present invention, a plasticizer is included in the polymer formulation to improve the film quality of the lactide polymer. More particularly, plasticizers reduce the melt viscosity at a given temperature of poly(lactide), which assists in processing and extruding the polymer at lower temperatures and may improve flexibility and reduce cracking tendencies of the finished film and also improves impact and tear resistance of the film and decreases noise.

A plasticizer is useful in concentration levels of about 1 to 40 percent by weight based on the weight of polymer. Preferably, a plasticizer is added at a concentration level of about 5 to 25 percent by weight. Most preferably, a plasticizer is added at a concentration level of about 8 to 25 percent by weight.

Selection of a plasticizing agent requires screening of many potential compounds and consideration of several criteria. For use in a biodegradable film the preferred plasticizer is to be biodegradable, non-toxic and compatible with the resin and relatively nonvolatile.

Plasticizers in the general classes of alkyl or aliphatic esters, ether, and multi-functional esters and/or ethers are preferred. These include alkyl phosphate esters, dialkylether diesters, tricarboxylic esters, epoxidized oils and esters, polyesters, polyglycol diesters, alkyl alkylether diesters, aliphatic diesters, alkylether monoesters, citrate esters, dicarboxylic esters, vegetable oils and their derivatives, and esters of glycerine. Most preferred plasticizers are tricarboxylic esters, citrate esters, esters of glycerine and dicarboxylic esters. Citroflex A4® from Morflex is particularly useful. These esters are anticipated to be biodegradable. Plasticizers containing aromatic functionality or halogens are not preferred because of their possible negative impact on the environment.

For example, appropriate non-toxic character is exhibited by triethyl citrate, acetyltriethyl citrate, tri-n-butyl citrate, acetyltri-n-butyl citrate, acetyltri-n-hexyl citrate, n-butyltri-n-hexyl citrate and dioctyl adipate. Appropriate compatibility is exhibited by acetyltri-n-butyl citrate and dioctyl adipate. Other compatible plasticizers include any plasticizers or combination of plasticizers which can be blended with poly(lactide) and are either miscible with poly(lactide) or which form a mechanically stable blend. Corn oil and mineral oil were found to be incompatible when used alone with poly(lactide) because of phase separation (not mechanically stable) and migration of the plasticizer.

Volatility is determined by the vapor pressure of the plasticizer. An appropriate plasticizer must be sufficiently non-volatile such that the plasticizer stays substantially in the resin formulation throughout the process needed to produce the film. Excessive volatility can lead to fouling of process equipment, which is observed when producing films by melt processing poly(lactide) with a high lactide content. Preferred plasticizers should have a vapor pressure of less than about 10 mm Hg at 170° C., more preferred plasticizers should have a vapor pressure of less than 10 mm Hg at 200° C. Lactide, which is not a preferred plasticizer, has a vapor pressure of about 40 mm Hg at 170° C. Example 6 highlights useful plasticizers for the present invention.

Internal plasticizers, which are bonded to the poly(lactide) may also be useful. Epoxides provide one method of introducing an internal plasticizer.

In a preferred composition, nucleating agents may be incorporated during polymerization. Nucleating agents may include selected plasticizers, finely divided minerals, organic compounds, salts of organic acids and imides and finely divided crystalline polymers with a melting point above the processing temperature of poly(lactide). Examples of useful nucleating agents include talc, sodium salt of saccharin, calcium silicate, sodium benzoate, calcium titanate, boron nitride, copper phthalocyanine, isotactic polypropylene, crystalline poly(lactide) and polybutylene terephthalate.

In a preferred composition, fillers may be used to prevent blocking or sticking of layers or rolls of the film during storage and transport. Inorganic fillers include clays and minerals, either surface modified or not. Examples include talc, diatomaceous earth, silica, mica, kaolin, titanium dioxide, perlite, and wollastonite. Preferred inorganic fillers are environmentally stable and non-toxic.

Organic fillers include a variety of forest and agricultural products, either with or without modification. Examples include cellulose, wheat, starch, modified starch, chitin, chitosan, keratin, cellulosic materials derived from agricultural products, gluten, nut shell flour, wood flour, corn cob flour, and guar gum. Preferred organic fillers are derived from renewable sources and are biodegradable. Fillers may be used either alone or as mixtures of two or more fillers. Examples 3 and 4 highlight useful anti-blocking fillers for the present invention. Surface treatments such as corona and flame treatments may also be used to reduce blocking.

Pigments or color agents may also be added as necessary. Examples include titanium dioxide, clays, calcium carbonate, talc, mica, silica, silicates, iron oxides and hydroxides, carbon black and magnesium oxide.

In the manufacture of the melt-stable lactide polymer compositions of the present invention, the reaction to polymerize lactide is catalyzed. Many catalysts have been cited in literature for use in the ring-opening polymerization of cyclic esters. These include but are not limited to: $SnCl_2$, $SnBr_2$, $SnCl_4$, $SnBr_4$, aluminum alkoxides, tin alkoxides, zinc alkoxides, SnO, PbO, Sn (2-ethyl hexanoates), Sb (2-ethyl hexanoates), Bi (2-ethyl hexanoates), Na (2-ethyl hexanoates) (sometimes called octoates), Ca stearates, Mg stearates, Zn stearates, and tetraphenyltin. Applicants have also tested several catalysts for polymerization of lactide at 180° C. which include: tin(II) bis(2-ethyl hexanoate) (commercially available from Atochem, as Fascat 2003, and Air Products as DABCO T-9), dibutyltin diacetate (Fascat 4200®, Atochem), butyltin tris(2-ethyl hexanoate) (Fascat 9102®, Atochem), hydrated monobutyltin oxide (Fascat 9100®, Atochem), antimony triacetate (S-21, Atochem), and antimony tris(ethylene glycoxide) (S-24, Atochem). Of these catalysts, tin(II) bis(2-ethyl hexanoate), butyltin tris(2-ethyl hexanoate) and dibutyltin diacetate appear to be most effective.

Applicants have found the use of catalysts to polymerize lactide significantly affects the stability of the resin product. It appears the catalyst as incorporated into the polymer also is effective at catalyzing the reverse depolymerization reaction and at catalyzing hydrolysis. Example 10 details the effect of residual catalyst on degradation. To minimize this negative effect, in a preferred composition, the residual catalyst level in the resin is present in a molar ratio of initial monomer-to-catalyst greater than about 3,000:1, preferably greater than about 5,000:1 and most preferably greater than about 10,000:1. Applicants believe a ratio of about 20,000:1 may be used, but polymerization will be slow. Optimization of catalyst levels and the benefits associated therewith are detailed in Example 20. Applicants have found that when the catalyst level is controlled within these parameters, catalytic activity is sufficient to polymerize the lactide while sufficiently low to enable melt-processing without adverse effect when coupled with low residual monomer level and low water concentration as described above in polymers of molecular weight between 10,000 to about 300,000. It is believed in most applications the addition of a stabilizing agent may be unnecessary if the catalyst level is optimized.

Applicants have also found that catalyst concentration may be reduced subsequent to polymerization by precipitation from a solvent. Example 21 demonstrates potential catalyst removal by precipitation from a solvent. This produces a resin with reduced catalyst concentration. In an alternative embodiment, the catalyst means for catalyzing the polymerization of lactide to form the poly(lactide) polymer chains which was incorporated into the melt-stable lactide polymer composition during polymerization is deactivated by including in the melt-stable lactide polymer composition a catalyst deactivating agent in amounts sufficient to reduce catalytic depolymerization of the poly(lactide) polymer chains. Example 11 details the benefits of utilizing a catalyst deactivating agent. Such catalyst-deactivating agents include hindered, alkyl, aryl and phenolic hydrazides, amides of aliphatic and aromatic mono- and dicarboxylic acids, cyclic amides, hydrazones and bishydrazones of aliphatic and aromatic aldehydes, hydrazides of aliphatic and aromatic mono- and dicarboxylic acids, bis-acylated hydrazine derivatives, and heterocyclic compounds. A preferred metal deactivator is Irganox®MD1024 from Ciba-Geigy. Biodegradable metal deactivators are particularly preferred.

In an alternative embodiment, the catalyst concentration is reduced to near zero by utilizing a solid-supported catalyst to polymerize lactide. The feasibility of utilizing such a catalyst is detailed in Example 8. It is believed catalysts which may be utilized include supported metal catalysts, solid acid catalysts, acid clays, alumina silicates, alumina, silica and mixtures thereof.

In a preferred composition, the catalyst usage and/or deactivation is controlled to reduce depolymerization of the poly(lactide) polymer during melt-processing to less than about 2 percent by weight generation of lactide from a devolatilized sample in the first hour at 180° C. and atmospheric pressure. More preferably, the amount of lactide generated is less than about 1 percent by weight in the first hour and most preferably less than about 0.5 percent by weight in the first hour.

A preferred melt-stable lactide polymer composition is the reaction product of polymerization of lactide at a temperature greater than about 160° C. Applicants have found that polymerization at higher temperatures result in a characteristically different polymer which is believed to have improved melt stability due to increased transesterification during polymerization. The benefits of higher temperature polymerization are detailed in Example 12.

Melt-Stable Lactide Polymer Process

The process for the manufacture of a melt-stable lactide polymer comprises the steps of first providing a lactide mixture wherein the mixture contains above about 9 percent by weight to about 50 percent by weight meso-lactide and about the remaining percent by weight being L-lactide, D-lactide or mixtures thereof. Such purified lactide stream may be such as that produced in the process disclosed by Gruber et al., although the source of lactide is not critical to the present invention.

The lactide mixture is polymerized to form a lactide polymer or poly(lactide) with some residual unreacted monomer in the presence of a catalyst means for catalyzing the polymerization of lactide to form poly(lactide). Catalysts suitable for such polymerization have been listed previously. The concentration of catalysts utilized may be optimized as detailed in the following examples and discussed previously.

In a preferred embodiment, a stabilizing agent, which may be an antioxidant and/or a water scavenger is added to the lactide polymer. It is recognized that such stabilizing agents may be added simultaneously with or prior to the polymerization of the lactide to form the lactide polymer. The stabilizing agent may also be added subsequent to polymerization.

As previously disclosed, the catalyst usage is adjusted and/or deactivation agent is added in a sufficient amount to reduce depolymerization of poly(lactide) during melt-processing to less than 2 percent by weight generation of lactide from a devolatilized sample in the first hour at 180° C. and atmospheric pressure. More preferably, the stabilizing agent controls lactide generation to less than 1 percent by weight and most preferably less than 0.5 percent by weight in the first hour at 180° C. and atmospheric pressure. Alternatively, the control of catalyst concentration to optimize the balance between necessary catalytic activity to produce poly(lactide) versus the detrimental effects of catalytic depolymerization or degradation of the lactide polymer may be utilized to obviate the need for adding a stabilizing agent.

The lactide polymer is then devolatilized to remove unreacted monomer which may also be a by-product of decomposition reactions or the equilibrium-driven depolymerization of poly(lactide). Any residual water which may be present in the polymer would also be removed during devolatilization, although it is recognized that a separate drying step may be utilized to reduce the water concentration to less than about 2,000 parts-per-million. The devolatilization of the lactide polymer may take place in any known devolatilization process. The key to selection of a process is operation at an elevated temperature and usually under conditions of vacuum to allow separation of the volatile components from the polymer. Such processes include a stirred tank devolatilization or a melt-extrusion process which includes a devolatilization chamber and the like. An inert gas sweep is useful for improved devolatization.

In a preferred process for manufacture of a melt-stable lactide polymer composition, the process also includes the step of adding a molecular weight control agent to the lactide prior to catalyzing the polymerization of the lactide. For example, molecular weight control agents include active hydrogen-bearing compounds, such as lactic acid, esters of lactic acid, alcohols, amines, glycols, diols and triols which function as chain-initiating agents. Such molecular weight control agents are added in sufficient quantity to control the number average molecular weight of the poly(lactide) to between about 10,000 and about 300,000.

Next referring to FIG. 1 which illustrates a preferred process for producing a melt-stable lactide polymer composition. A mixture of lactides enters a mixing vessel (3) through a pipeline (1). A catalyst for polymerizing lactide is also added through a pipeline (13). Within mixing vessel (3) a stabilizing agent may be added through a pipeline (2). A water scavenger may also be added through the pipeline (2). The stabilized lactide mixture is fed through a pipeline (4) to a polymerization process (5). The polymerized lactide or lactide polymer leaves the polymerization process through a pipeline (6). The stream is fed to a second mixing vessel (8) within which a stabilizing agent and/or catalyst deactivating agent may be added through a pipeline (7). The stabilized lactide polymer composition is then fed to a devolatilization process (10) through a pipeline (9). Volatile components leave the devolatilization process through a pipeline (11) and the devolatilized lactide polymer composition leaves the devolatilization process (10) in a pipeline (12). The devolatilized lactide composition is fed to a resin-finishing process (14). Within the resin-finishing process the polymer is solidified and processed to form a pelletized or granular resin or bead. Applicants recognize the polymer may be solidified and processed to form resin or bead first, followed by devolatilization. The resin is then fed to a drying process (16) by conveyance means (15). Within the drying process (16) moisture is removed as a vapor through pipeline (17). The dried lactide polymer resin leaves the drying process (16) by a conveyance means (18) and is fed to a melt-processing apparatus (19). Within the melt-processing apparatus (19) the resin is converted to a useful article as disclosed above. The useful article leaves the melt-processing apparatus (19) through a conveyance means (20).

The following examples further detail advantages of the system disclosed herein:

The following table illustrates critical data:

TABLE 1

| Compounding: Twin Screw conditions | Cast Film: Killion Conditions |
|---|---|
| zone 1: 150° C. | zone 1: 286° F. |
| zones 2–8: 180° C. | zone 2: 320° F. |
| zones 9 % 10: 170° C. | zone 3: 320° F. |
| melt temp: 194° C. | zone 4: 315° F. |
| die pressure: 44 psi | adaptor: 310° F. |
| amps: 17.8–20.0 | die temp: 310° F. |
| screw rpm: 300 | pressure: 1340 psi |
| Pressure in devolatization zone 200 mm hg | screw rpm: 20.2 |

The following table illustrates the results. It is noted that blends of poly(caprolactone) and poly(lactide) are more flexible than unblended poly(lactide) as shown by the increased elongation. This is significant for flexible films as well as other products where decreased brittleness is required.

TABLE 2

| Film: | Mn: | Mw: | PDI: | % Lactide | Break Str. (kpsi) | Modulus (kpsi) |
|---|---|---|---|---|---|---|
| Example 1 PLA | 66662 | 157866 | 2.37 | 0.19 | 7.9 | 317 |
| Example 2 PLA + 12.8% tone | 68564 | 170697 | 2.49 | 0.33 | 8.6 | 350 |
| Example 3 PLA + 25.6% tone | 95355 | 240973 | 2.53 | 0.08 | N/A | N/A |
| Example 4 PLA + 38.6% tone & 10% citro.A-4s | 87013 | 221583 | 2.55 | 0.36 | N/A | N/A |
| Example 5 PLA + 19% tone & 10% citro.A-4s | 63024 | 161643 | 2.56 | 0.35 | N/A | N/A |

| Injection Molded Test Bars: | Break Str. (kpsi) | Modulus (kpsi) | Elongation at break (%) |
|---|---|---|---|
| Example 6 PLA | 7.2 | 493 | 5.6 + −1.9 |
| Example 7 12.7% tone + PLA | 6.6 | 403 | 227 + −52 |
| Example 8 25.6% tone + PLA | 3.2 | 340 | 250 + −133 |
| Example 9 38.6% tone + PLA | 2.7 | 332 | 149 + −58 |

EXAMPLE 1

Blended Film

Polycaprolactone commercially available as TONE 787 from Union Carbide was added/mixed with poly(lactide) having a number average molecular weight of 157,900, a residual lactide concentration of 0.19%, a meso-lactide concentration of about 10% and a water concentration of less than about 500 ppm on a Leistritz twin screw extruder at 12.8%, 25.6%, 38.4% by weight to poly(lactide). These blends were injection molded into standard ASTM test bars using a Cincinnati Milacron Vista Sentry VST-55 molding press and physical properties were measured and tensiles tested on the bars. The above blends were also extruded into cast film on a Killion extruder with a sheet die, die gap 0.035", with 0.25% by weight Celite Super Floss diatomaceous earth for the purpose of an anti-block agent.

EXAMPLE 2

Orientation of a Poly(lactide)

To demonstrate the ease and benefit of making oriented poly(lactide) film, an experiment was done to make sheets using poly(lactide) and orientating the sheet to different degrees. The polymer selected had 280,000 to 400,000 weight average molecular weight, 100,000 to 150,000 number average molecular weight, lactide concentration lower than 1%, meso level of about 10 to 20%, and a moisture level lower than about 500 ppm.

A sheet was cast using a 2" diameter single barrier flight screw Davis-Standard extruder with a 24:1 L/D. The die was 24" wide with an adjustable gap. The casting roll was 30" wide and 24" in diameter and equipped with temperature controls. After casting, the sheet was oriented in both the machine (MD) and transverse (TD) directions.

The MD orienter consisted of six 30" wide rolls and five temperature control zones: roll 1 and 2 were for preheat, roll 3 for slow draw, roll 4 for fast draw, roll 5 for heat setting, and roll 6 for cooling the sheet. Draw ratios up to 20 were used for the MD orientation.

The TD orienter was a standard tenter frame with a 3 zone oven. The feed width range for the tenter was 8–48" and the output width range was 16–62". Following the orientation section was a slitter/winder.

Typical conditions used in extruding the sheet are shown below:

| Extruder | zone 1 | 350 to 400° F. | (177–204° C.) |
|---|---|---|---|
|  | zone 2 | 360 to 400° F. | (182–204° C.) |
|  | zone 3 | 340 to 350° F. | (171–188° C.) |
| Melt pip/adapters |  | 330 to 350° F. | (166–177° C.) |
| Die zones |  | 330° F. |  |
| Head pressure |  | 1640 to 2280 psi |  |
| Screw speed 45 to 75 rpm |  |  |  |

Melt strength at the die was very good at 330° F. (166° C.). The die was positioned about 0.5 inch off the cast roll, which was run between 112° and 126° F. An air knife was used to pin the melt against the cast roll to reduce neck-in.

Conditions found useful for machine direction orientation of poly(lactide) were temperatures of 65° C. for the preheat rolls, 65° C. and 72° C. for the slow draw roll at low draw ratios and high draw ratios respectively, 65° C. for the fast draw roll, 45° C. for the heat roll, and 20° C. for the cooling roll.

The gap between the slow and fast roll was set to the minimum possible. Orientation took place only slightly above the Tg to give a high degree of molecular alignment. Rolls were collected after MD orientation and some were used for TD orientation.

Conditions for transverse direction orientation were 63° C. for the preheat zone, 70° C. for the stretching zone, and 67° C. for the annealing zone. Ambient air was circulated at the oven exit to cool the oriented sheet before winding.

The poly(lactide) oriented very well, being easily curved over the rolls and requiring lower process temperatures than standard plastic. The products made were:

|  | MD | TD | Approx. Thickness |
|---|---|---|---|
| Sample 1 MD | 0 | 0 | 5 mil |
| Sample 2 MD | 3.2 | 0 | 5 mil |
| Sample 3 MD | 3.5 | 4.3 | 1 mil |
| Sample 4 MD | 3.5 | 2.0 | 2 mil |
| Sample 5 MD | 1.5 | 2.9 | 9 mil |
| Sample 6 MD | 1.5 | 2.0 | 13 mil |

Samples 1, 2 and 3 were tested for tensile and elongation according to ASTM D882 and tear resistance according to ASTM D689. The results are shown below:

|  | Tensile Strength at break (lb/in/mil) | Elongation at break (%) | Tear Strength (g-cm) |
|---|---|---|---|
| Sample 1 | 6.9 | 4.3 | 40 |
|  | 7.4 | 4.8 | 40 |
| Sample 2 | 15.8 | 85.1 | 16 |
|  | 6.9 | 3.2 | 40 |
| Sample 3 | 23.9 | 89.3 | 32 |
|  | 10.5 | 160 | 128 |

As the data in the table shows, the strength and flexibility of the poly(lactide) film can be greatly increased by orientation.

EXAMPLE 3

Anti-Block Aids

The use of anti-block aids can increase the resistance of two poly(lactide) films to stick together at elevated temperatures. This was demonstrated using poly(lactide) having a weight average molecular weight of 165,000, a residual lactide level of about 0.1%, a meso level of about 10%, and a moisture level about 60 ppm. The anti-block aid was diatomaceous earth having a median particle size of 3.5 microns (CELITE SUPER FLOSS from Celite) which was dried to a moisture level of about 400 ppm. The diatomaceous earth and poly(lactide) were blended in a twin screw extruder at different levels of anti-block aid and pelletized. The pellets were converted into film using the single screw extruder as in Example 2. The films were tested for resistance to adhering to one another by placing two films together with a 92 gram weight on top in an oven set at 60° C. for 2 hours. A failure was when the films could not be separated after being removed from the oven. The results are shown in the following table.

TABLE 3

| Sample I.D. | % Celite Super Floss | Blocking Test 1 | Blocking Test 2 |
|---|---|---|---|
| 2113-90-0 | 0.0 | Fused | Fused |
| 2113-90-1 | 4.1 | None | None |
| 2113-90-2 | 7.9 | Some tiny pts. stuck | None |
| 2113-90-3 | 1.8 | Some pts. stuck | None |
| 2113-90-4 | 0.9 | Some pts. stuck | None |
| 2113-90-5 | 0.45 | Some pts. stuck | None |

EXAMPLE 4

Anti-Blocking Agents

Two injection molded disks, 2.5 inch diameter, were placed together with a 94 gram weight on top and held at 50° for 24 hours. The disks had the following agents compounded therein. The disks were then cooled to room temperature and pulled apart by hand and ranked for blocking characteristics (considerable, slight and none). The following are the results:

TABLE 4

| AGENTS | |
|---|---|
| Poly(lactide) control | considerable |
| 22% wheat gluten | none |
| 10% wheat gluten | slight |
| 22% pecan shell | none |
| 15% pecan shell | slight |
| 23% wollastonite | slight |
| 28% Ultratalc 609 | none |
| 23% Ultratalc 609 | none |
| 28% Microtuff F talc | slight |
| 22% Microtuff F talc | slight |
| 14% Microtuff F talc | slight |
| 2% Microtuff F talc | considerable |

EXAMPLE 5

Heat Sealability of a Poly(lactide) Film:

Poly(lactide) with a weight average molecular weight of 160,000, a meso-lactide content of 8 to 12%, and a moisture level of about 200 ppm, was extruded into a film using the same method as Example 2.

Two pieces of the poly(lactide) film were heat sealed in an Accuseal Heat Sealer Model 30 having heated platens of a dimension of ¼"×25". The temperature and dwell time were varied to find the minimum required to form a bond between the films. Pressure was 40 psi. Bond strength was estimated by pulling the two films apart 10 seconds after sealing and judging pass or fail. Either the films tore before the bond failed (pass) or the films separated at the bondline (fail). Results are shown below:

TABLE 5

| Time (sec) | Temperature (C.°) | | | | | | | | | |
|---|---|---|---|---|---|---|---|---|---|---|
| | 30 | 40 | 50 | 60 | 65 | 70 | 75 | 80 | 85 | 90 |
| 1 | F | F | | | | | | | | |
| 2 | | | F | F | F | P | P | | | |
| 3 | | | | F | | | | P | P | |
| 4 | | | | | P | | | | | P |
| 5 | | | | | | | | P | | |
| 6 | | | | | | | | | | P |

Sealing conditions of 70° C. at a line pressure of 40 psi for a 2 second dwell time were found to be sufficient for forming a good bond between the two poly(lactide) films.

EXAMPLE 6

Plasticizer Agents

Dried pellets of devolatilized poly(lactide) were processed in a twin screw extruder to allow compounding of various plasticizing agents. The strands leaving the extruder were cooled in a water trough and chopped into pellets. Samples of the pellets were heated at 20° C./minute to 200° C. in a DSC apparatus, held at 200° C. for 2 minutes and rapidly cooled to quench the samples. The quenched samples were then reheated in the DSC apparatus increasing at 20° C./minute to determine the glass transition temperature. These samples were compared to a polymer with no plasticizer. The effect of the plasticizer on the glass transition temperature is shown in the table below. Glass transition temperatures are taken at the mid-point of the transition.

TABLE 6

| SAMPLE | $T_g$(C) | Change in $T_g$/wt. percent additive |
|---|---|---|
| Control | 54.8 | — |
| 8% Dioctyl adipate | 35.0 | 2.5 |
| Control + 40% silica | 54.5 | — |
| Control + 40% silica + 5% dioctyl adipate | 36.0 | 3.7 |
| Control | 54.6 | — |
| 6% Citroflex A-4* | 42.6 | 2.0 |
| 12% Citroflex A-4 | 31.4 | 1.9 |
| Control | 59.3 | — |
| 1.6% Citroflex A-4 | 56.3 | 1.9 |
| 2.9% Citroflex A-4 | 53.1 | 2.1 |
| Control | 58.4 | — |
| 2.1% Citroflex A-4 | 56.1 | 1.1 |
| 3.4% Citroflex A-4 | 50.5 | 2.3 |
| Control | 61.6 | — |
| 18.6% Citroflex A-2 | 54.7 | 0.4 |
| 13.1% Citroflex B-6 | 52.4 | 0.7 |
| 12.6% Citroflex A-6 | 53.8 | 0.6 |

*Citroflex is a registered trademark of Morflex, Inc., Greensboro, NC. A-4 is the designation of a purified acetyltri-n-butyl citrate. A-2 is the designation of acetyltriethyl citrate, A-6 is the designation of acetyltri-n-hexyl citrate, and B-6 is the designation of n-butyryltri-n-hexyl citrate.

These results show the effectiveness of these plasticizers in reducing the glass transition temperature of poly(lactide).

The procedure above was tried using corn oil as a plasticizer. Visual observation showed the corn oil to be not compatible, forming a film on the surface. Corn oil and mineral oil were both not effective as a primary plasticizer with poly(lactide). They may still be useful as a secondary plasticizer, in combination with a compatible primary plasticizer.

EXAMPLE 7

Lactide and Poly(lactide) Equilibrium Concentrations

Experiments were conducted to determine the equilibrium concentration of lactide and poly(lactide) at different temperatures. In these experiments a sample of lactide was polymerized in the presence of a catalyst (tin (II) bis(2-ethyl hexanoate)) and held at a fixed temperature for 18 hours or greater. Beyond this time the residual monomer concentration is believed essentially constant. The content of residual monomer was determined by GPC analysis. GPC analysis was conducted with an Ultrastyragel® column from Waters Chromatography. The mobile phase was chloroform. A refractive index detector with molecular weight calibration using polystyrene standards was used. The GPC temperature was 35° C. Data analysis was completed using the software package Baseline, model 810, version 3.31.

Figure 2:
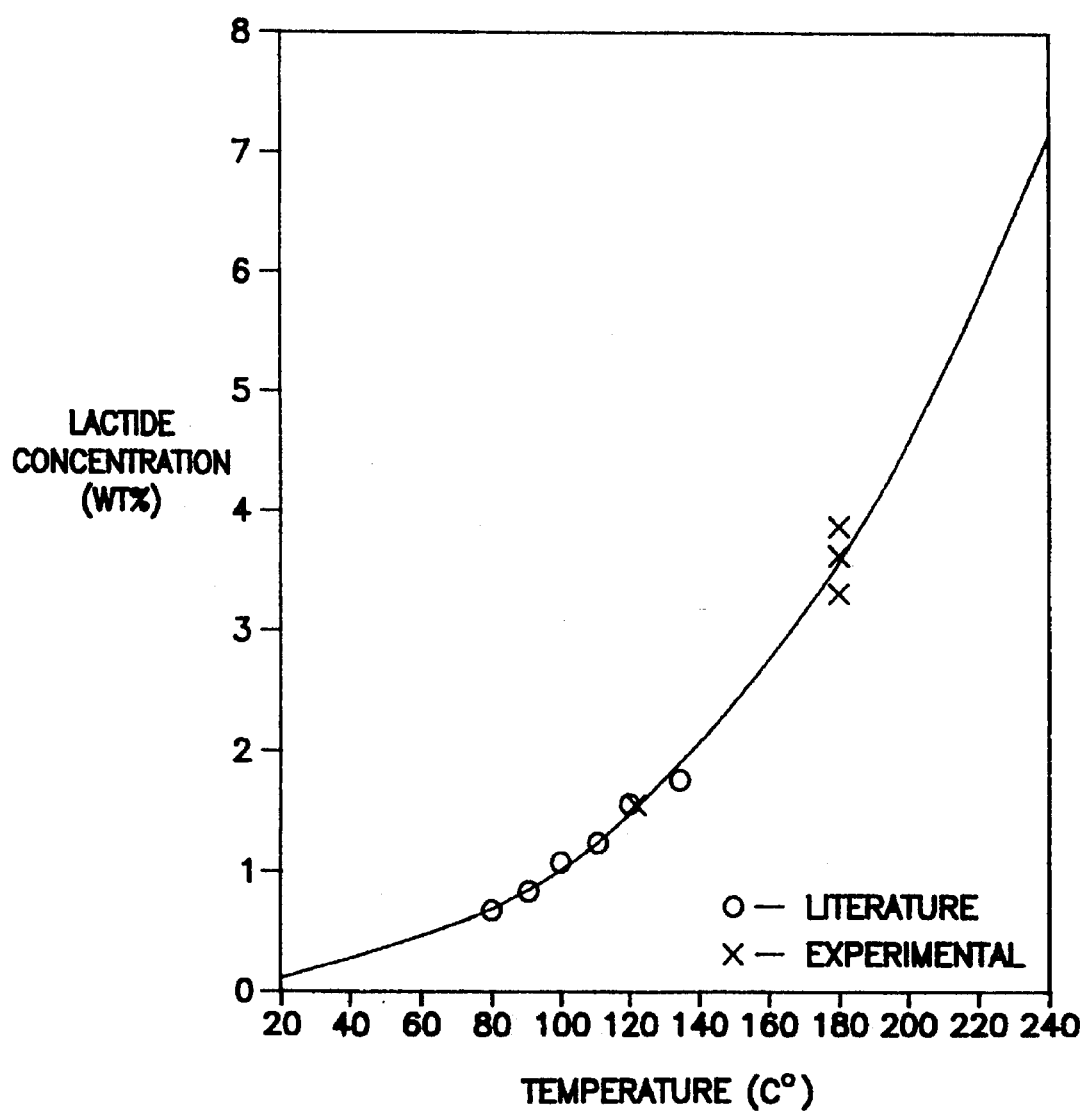
FIG. 2 is a graph showing the equilibrium relationship between lactide and poly(lactide) at various temperatures.

The results of tests conducted on several samples at various temperatures are summarized in the graph of FIG. 2 as indicated by X's on such graph. Also plotted on the graph of FIG. 2 are data points cited in A. Duda and S. Penczek, *Macromolecules*, vol. 23, pp. 1636–1639 (1990) as indicated by circles on the graph. As can be seen from the graph of FIG. 2, the equilibrium concentration, and thus the driving force behind the depolymerization of poly (lactide) to form lactide, increases dramatically with increased temperature. Thus, melt-processing at elevated temperatures results in degradation of the lactide polymer to form lactide on the basis of equilibrium alone. For example, lactide concentrations below about 2 percent cannot be directly obtained at temperatures of 140° C. or above due to the identified equilibrium relationship between lactide and poly(lactide).

EXAMPLE 8

Lactide Polymerization in the Presence of a Solid Supported Catalyst

Tin (II) Oxide 24 grams of L-lactide (melting point about 97° C.) and 6 grams of D,L-lactide (for the purposes of this invention, D,L-lactide has a melting point of about 126° C.) were combined in a round bottom flask with 0.033 grams of Tin (II) oxide, as a fine powder. This corresponds to the catalyst level of 852:1, molar ratio lactide to tin. The flask was then purged with dry nitrogen 5 times. This was lowered into an oil bath at 160° C. with magnetic stirring. Polymerization time was 8 hours.

Amberlyst 36

24 grams of L-lactide and 6 grams of D,L-lactide were combined in a round bottom flask with 1.06 grams of Amberlyst 36 resin beads. The flask was purged 5 times with dry nitrogen. The flask was lowered into an oil bath at 140° C. with magnetic stirring. Polymerization time was 8 hours. The resin had a stated proton content of 1 meq/gram dry weight resin. The resin was prepared by rinsing 2 times with 10 volumes dry methanol, then dried for several hours under high vacuum for several hours at 40° C.

The polymerization results are shown below:

TABLE 7

| Sample | Mn | Mw | PDI | % Conversion |
| --- | --- | --- | --- | --- |
| Tin (II) Oxide | 77,228 | 103,161 | 1.34 | 54.0 |
| Amberlyst | 1,112 | 1,498 | 1.34 | 73.5 |

EXAMPLE 9

Molecular Weight Relationship to Physical Properties of Lactide Polymers

Poly(lactide) samples with various molecular weights and optical compositions were prepared by polymerizing blends of L-lactide and meso-lactide at 180° C. under nitrogen in a 1-gallon sealed reactor. Tin(II) bis(2-ethyl hexanoate) catalyst was added at a monomer-to-catalyst ratio of 10,000:1. After about 1 hour the molten polymer was drained from the reactor using nitrogen pressure. The sample was poured into a pan and placed in a vacuum oven at about 160° C. for about 4 hours to bring the reaction to near equilibrium levels.

Portions of the samples were then dried under vacuum and processed in an injection molding apparatus (New Britain 75 from New Britain Machine Co.) to produce standard test bars for physical property testing. The results of physical property testing are shown in the following Table 8. The physical property tests were made according to ASTM methods D 638, D 256, and D 790. The reported results are the averages of several tests.

Samples of the test bars after injection molding were analyzed by GPC for molecular weight. Other portions of the test bars were reground and tested in a capillary viscometer to determine the melt-viscosity. These results are also included in Table 8.

Statistical analysis of the data revealed no correlations which were statistically significant between either optical composition or molecular weight and the mechanical properties of modulus, tensile strength, percentage elongation at break, notched Izod impact strength, flexural modulus, or flexural strength. The independence of these properties on molecular weight indicates that all of these samples were above a "threshold" molecular weight required to achieve the intrinsic properties of the polymer in a preferred composition.

The viscosity data show significant correlations with molecular weight. This dependence documents the practical limitation and necessity of controlling polymer molecular weight below an upper limit at which it is impractical to melt-process the polymer. At high molecular weight, high viscosity prevents processing by standard melt-processing equipment. Increases in temperature to reduce viscosity dramatically increase polymer degradation and lactide formation which is also unacceptable.

TABLE 8

| | | Molecular Weight | Viscosity at 173° C. (Pa · S) | | |
| --- | --- | --- | --- | --- | --- |
| Sample I.D. | Meso Lactide In Blend, Wt % | After Injection Weight | Final IV (dl/g) | Shear Rate 100 S$^{-1}$ | Shear Rate 1000 S$^{-1}$ |
| 6 | 40 | 41000 | 0.86 | 5.5 | 2.9 |
| 5 | 10 | 54000 | 0.88 | 10.4 | 7.2 |
| 4 | 20 | 59000 | 0.91 | 10.4 | 7.2 |
| 8 | 10 | 64000 | 1.02 | 15.7 | 10.0 |
| 9 | 40 | 68000 | 0.97 | 12.6 | 8.1 |
| 7 | 20 | 71000 | 1.16 | 36.0 | 12.9 |
| 10 | 20 | 83000 | 1.19 | 35.8 | 15.8 |

| Mechanical Properties of Injection Molded Samples | | | | | |
| --- | --- | --- | --- | --- | --- |
| Sample I.D. | Modulus MPSI | Tensile Strength (Yld) PSI | % Elongation at Break | IZOD Impact ft · lb./in | Flexural Modulus MPSI | Flexural Strength PSI |
| 6 | 0.55 | 6600 | 3.3 | 0.39 | 0.53 | 11300 |
| 5 | 0.56 | 7800 | 3.5 | 0.46 | 0.54 | 12500 |
| 4 | 0.56 | 7600 | 3.9 | 0.32 | 0.53 | 12500 |
| 8 | 0.55 | 7700 | 3.4 | 0.47 | 0.53 | 12400 |
| 9 | 0.59 | 6700 | 3.1 | 0.42 | 0.52 | 10600 |
| 7 | 0.56 | 7400 | 3.3 | 0.45 | 0.51 | 12400 |
| 10 | 0.55 | 6700 | 3.0 | 0.47 | 0.52 | 9900 |

EXAMPLE 10

Effect of Residual Catalyst on Polymer Degradation

Polymer samples were prepared at four levels of catalyst, corresponding to monomer to catalyst molar ratios of 5,000:1, 10,000:1, 20,000:1, and 40,000:1. The catalyst utilized was tin (II) bis(2-ethyl hexanoate). These samples were then subjected to heating in a TGA apparatus (TA Instruments, Inc., model 951 thermogravimetric analyzer with a DuPont 9900 computer support system) with a nitrogen purge. Isothermal conditions of 200° C. for 20 minutes were used. The samples were then analyzed by GPC with a viscosity-based detector and a universal calibration curve to determine the extent of breakdown in molecular weight. The GPC apparatus for this test was a Viscotek Model 200 GPC and a Phenomenex column. The TGA analysis typically resulted in about a 5 percent loss in weight and molecular weight drops of 0 to 70 percent.

The number average molecular weights were converted to a milliequivalent per kilogram basis (1,000,000/Mn) in order to calculate a rate of chain scission events. The results below represent averages of 2–4 replicates on each of the four samples.

TABLE 9

| Catalyst level (monomer/catalyst) | Scission Rate (meq/kg*min) |
|---|---|
| 5,000 | 1.33 |
| 10,000 | 0.62 |
| 20,000 | 0.44 |
| 40,000 | 0.12 |

The rate of chain scission was directly proportional to the residual catalyst level, demonstrating the detrimental effect of catalyst activity on melt-stability under conditions similar to melt-processing. This instability, however, is distinguished from the instability due to the equilibrium relationship between lactide and poly(lactide) detailed in Example 7, in that loss of molecular weight due to catalytic depolymerization by chain scission is evident.

EXAMPLE 11

Catalyst Deactivation Experiment

Two runs were made in a laboratory Parr reactor. Lactide feed was 80 percent L-lactide and 20 percent D,L-lactide. Molecular weight was controlled by adding a small quantity of lactic acid, the target molecular weight was 80,000 Mn.

Lactide was charged to the reactor as a dry mix, the reactor was purged 5 times with nitrogen, and heated up to 180° C. At this point catalyst (5000:1 initial monomer to catalyst molar ratio, Fascat® 2003) was charged through a port in the top of the reactor. The reaction was allowed to proceed for 70 minutes at 180° C., with mechanical agitation. Conversion at this point was 93–94 percent, close to the equilibrium value at 180° C. of 96 percent poly(lactide) from FIG. 2. This point is considered t-zero, designating the completion of the polymerization reaction and the beginning of the mixing time.

In the control experiment, a sample was taken and the mixture was held at temperature with continued agitation. Samples were taken periodically through a port in the reactor bottom. After 4 hours the reactor was drained.

In the example experiment, a sample was taken and 0.25 weight percent of a metal deactivator (Irganox® MD 1024®) was added through the catalyst addition port. The mixture was held at temperature with continued agitation and samples were withdrawn periodically. The reactor was drained after 4 hours.

GPC analysis (utilizing the method of Example 7) for these samples was divided into three parts: polymer with molecular weight over 4,000 (for which the Mn and Mw numbers are reported), the percent oligomers (comprising the region with molecular weight greater than lactide but less than 4,000, as distinguished from oligomers as defined by Loomis to include only oligomers up to a molecular weight of 450), and percent lactide (residual monomer). The structure of the oligomers was not certain, but it is believed they were primarily cyclic structures. It is also believed that the metal deactivator, if unreacted, will elute with the oligomer fraction. Quantification of the oligomer fraction is difficult, because the GPC trace is near the baseline in this region.

The analysis of the polymer samples as withdrawn from the reactor at various time intervals for the control and experimental compositions are shown below in Table 10.

TABLE 10

| Control | Mn | Mw | % Polymer | % Oligomer | % Monomer |
|---|---|---|---|---|---|
| t-zero | 67,100 | 119,500 | 94 | 0 | 6.0 |
| 0.5 hr | 62,500 | 119,000 | 95 | 0.7 | 3.9 |
| 1.0 hr | 61,500 | 116,100 | 96 | 0 | 3.6 |
| 1.5 hr | 56,000 | 111,600 | 95 | 1.5 | 3.3 |
| 2.0 hr | 57,600 | 110,900 | 96 | 0.9 | 3.1 |
| 4.0 hr | 51,400 | 105,400 | 94 | 3.3 | 3.1 |

| Test | Mn | Mw | % Polymer | % Oligomer | % Monomer |
|---|---|---|---|---|---|
| t-zero | 63,200 | 110,700 | 93 | 3.5 | 3.8 |
| 0.5 hr | 52,100 | 108,600 | 92 | 4.6 | 2.9 |
| 1.0 hr | 52,700 | 109,200 | 92 | 4.9 | 2.8 |
| 1.5 hr | 53,400 | 107,200 | 93 | 4.0 | 3.1 |
| 2.0 hr | 59,700 | 111,100 | 94 | 0.6 | 5.8 |
| 4.0 hr | 51,200 | 107,300 | 91 | 6.1 | 3.3 |

The samples were then ground and placed in a 120° C. oven under vacuum (pressure 0.1 inch Hg) for 14 hours. Sample analyses after this treatment are shown below in Table 11.

TABLE 11

| Control | Mn | Mw | % Polymer | % Oligomer | % Monomer |
|---|---|---|---|---|---|
| t-zero | 45,500 | 88,500 | 98 | 2.2 | 0.0 |
| 0.5 hr | 45,000 | 88,700 | 98 | 2.0 | 0.0 |
| 1.0 hr | 43,900 | 87,200 | 98 | 2.0 | 0.0 |
| 1.5 hr | 42,600 | 84,000 | 98 | 2.2 | 0.0 |
| 2.0 hr | 42,000 | 85,200 | 97 | 3.2 | 0.0 |
| 4.0 hr | 41,900 | 82,800 | 98 | 2.0 | 0.0 |

| Test | Mn | Mw | % Polymer | % Oligomer | % Monomer |
|---|---|---|---|---|---|
| t-zero | 39,300 | 76,700 | 96 | 4.0 | 0.0 |
| 0.5 hr | 43,900 | 85,100 | 98 | 2.4 | 0.0 |
| 1.0 hr | 55,300 | 98,600 | 96 | 3.8 | 0.0 |
| 1.5 hr | 48,400 | 96,200 | 95 | 4.5 | 0.0 |
| 2.0 hr | 48,900 | 101,900 | 95 | 5.0 | 0.0 |
| 4.0 | 50,600 | 101,900 | 94 | 5.6 | 0.0 |

In all cases the polymer was completely devolatilized (0.0 percent residual lactide monomer). The data also clearly show that the metal deactivator reduced the degradation of polymer during the devolatilization step (as indicated by the greater loss in Mn for the control samples from Table 9 to Table 10 versus the Test samples). One hour of mixing appears to be long enough to develop most of the benefit.

The samples were stored at room temperature under nitrogen for about 1 week and reanalyzed, as shown below in Table 12.

TABLE 12

| Control | Mn | Mw | % Polymer | % Oligomer | % Monomer |
|---|---|---|---|---|---|
| t-zero | 33,500 | 71,000 | 100 | 0.1 | 0.0 |
| 0.5 hr | 43,400 | 95,800 | 99 | 1.0 | 0.0 |
| 1.0 hr | 44,900 | 96,300 | 100 | 0.1 | 0.0 |
| 1.5 hr | 45,900 | 95,000 | 100 | 0.0 | 0.0 |

TABLE 12-continued

| | | | | | |
|---|---|---|---|---|---|
| 2.0 hr | 45,900 | 94,100 | 100 | 0.2 | 0.0 |
| 4.0 hr | 43,100 | 90,100 | 99 | 1.3 | 0.0 |

| Test | Mn | Mw | % Polymer | % Oligomer | % Monomer |
|---|---|---|---|---|---|
| t-zero | 44,600 | 84,900 | 100 | 0.0 | 0.0 |
| 0.5 hr | 45,300 | 90,600 | 99 | 1.2 | 0.0 |
| 1.0 hr | 47,800 | 100,000 | 98 | 2.4 | 0.0 |
| 1.5 hr | 46,600 | 98,900 | 96 | 3.5 | 0.0 |
| 4.0 | 57,700 | 110,200 | 96 | 4.0 | 0.3 |

Equilibrium lactide levels are estimated to be less than 0.2 weight percent at room temperature. Consistent with that, essentially no lactide was observed in any of the samples (detection limit about 0.1 weight percent). The oligomer content in the non-stabilized samples declined and some increase in molecular weight was noted, perhaps due to reincorporation of the (cyclic) oligomers into the polymer. The oligomer depletion reaction was inhibited in the stabilized polymers, with the extent of inhibition dependent on the length of time that the additive was mixed.

The samples were then reheated to 180° C. in sealed vials and held for one hour as a simulation of melt-processing. Analysis of the samples after the heat treatment is given below in Table 13.

TABLE 13

| | Mn | Mw | % Polymer | % Oligomer | % Monomer |
|---|---|---|---|---|---|
| Control | | | | | |
| t-zero | 23,900 | 60,000 | 88 | 8.4 | 4.0 |
| 0.5 hr | 23,900 | 59.600 | 90 | 7.7 | 2.7 |
| 1.0 hr | 23,700 | 58,800 | 88 | 9.3 | 2.7 |
| 1.5 hr | 24,700 | 58,000 | 86 | 10.0 | 3.8 |
| 2.0 hr | 26,100 | 56,400 | 90 | 6.8 | 2.7 |
| 4.0 hr | 24,800 | 58,700 | 92 | 6.6 | 1.9 |
| Test | | | | | |
| t-zero | 33,900 | 64,300 | 95 | 2.2 | 3.1 |
| 0.5 hr | 17,900 | 34,600 | 94 | 4.8 | 1.7 |
| 1.0 hr | 21,200 | 42,900 | 94 | 4.6 | 1.8 |
| 1.5 hr | 29,200 | 56,900 | 98 | 0.5 | 1.8 |
| 2.0 hr | missing | | | | |
| 4.0 hr | 35,700 | 71,400 | 95 | 3.7 | 1.7 |

The data for molecular weight show that if the metal deactivator is not mixed into the system long enough then it can have a detrimental impact on stability in the melt. The samples for which the mixing was at least 1.5 hours show no detrimental effect, and the 4 hour sample appears to be somewhat more stable than any of the others based on molecular weight alone. More importantly, the metal deactivator samples show significantly less lactide reformation than the control samples. This effect is gained even in the samples which were mixed for only 0.5 hour. The metals deactivated samples averaged only 1.8 percent lactide after one hour at 180° C., compared to an average of 3.0 percent lactide for the controls. The equilibrium level at 180° C. is about 3.6 percent from FIG. 2. Thus, the use of metal deactivators can reduce the troublesome reformation of lactide during melt-processing of the finished polymer.

EXAMPLE 12

Effect of Increased Polymerization Temperature on Polymer Characteristics

L-lactide (Boeringer Ingleheim, S-grade) was used as received, meso-lactide (PURAC) was purified by distillation to remove traces of D- and L-lactide. The melting point of the purified meso-lactide was 54° C. Lactide mixtures were made up to the following ratios: 100 percent L-lactide, 90/10 L-lactide/meso-lactide, 70/30 L-lactide/meso-lactide, 50/50 L-lactide/meso-lactide, and 100 percent meso-lactide. Catalyst level was 2,500:1 molar ratio of initial monomer to tin with the tin being tin(II) bis (2-ethyl hexanoate) (Fascat® 9002). Lactic acid was added as a molecular weight control agent to target a number average molecular weight of 50,000 (the same amount was added to all samples). Polymerization times were estimated to obtain conversions of 50 percent and 90 percent. For 120° C. this was 4 hours and 16 hours, respectively. For 180° C. these times were 10 minutes and 50 minutes, respectively. Below in Table 14 are the GPC results (method of Example 7) of tests on the polymer samples produced by this procedure.

TABLE 14

| L/meso | Temp | Mn | Mw | PDI | % Conv |
|---|---|---|---|---|---|
| 100% L | 120° C. | 31,014 | 33,774 | 1.09 | 53.2 |
| | | 45,864 | 52,574 | 1.15 | 87.1 |
| 100% L | 180° C. | 27,785 | 32,432 | 1.17 | 46.7 |
| | | 56,839 | 98.125 | 1.73 | 93.3 |
| 90/10 | 120° C. | 34,541 | 38,586 | 1.12 | 62.3 |
| | | 29,222 | 34,466 | 1.18 | 89.3 |
| 90/10 | 180° C. | 31,632 | 35,713 | 1.13 | 48.5 |
| | | 57.925 | 110,841 | 1.91 | 94.8 |
| 70/30 | 120° C. | 41,211 | 45.222 | 1.10 | 60.1 |
| | | 58,284 | 71,257 | 1.22 | 89.1 |
| 70/30 | 180° C. | 32,292 | 37,401 | 1.16 | 53.8 |
| | | 51,245 | 107,698 | 2.10 | 96.5 |
| 50/50 | 120° C. | 15,888 | 17,969 | 1.13 | 57.8 |
| | | 25,539 | 31,834 | 1.25 | 90.6 |
| 50/50 | 180° C. | 34,375 | 42,018 | 1.22 | 62.5 |
| | | 44,590 | 98,028 | 2.20 | 95.5 |
| 100% meso | 120° C. | 33,571 | 40,635 | 1.21 | 73.4 |
| | | 45,237 | 68,142 | 1.51 | 94.3 |
| 100% meso | 180° C. | 30,976 | 42,987 | 1.39 | 67.6 |
| | | 40,038 | 83,815 | 2.09 | 96.6 |

The results show that the ultimate number average molecular weight was not significantly affected by the temperature of polymerization, with an average of 41,000 at 120° C. and 50,000 at 180° C. This implies that each lactic acid molecule initiates about one polymer chain, regardless of temperature. The ultimate weight average molecular weight is, however, significantly affected by temperature. At 120° C. the weight average molecular weight averaged 52,000 and at 180° C. the average was 100,000. This is believed to be due to a relative increase in the rate of transesterification at 180° C. The polydispersity index (PDI) at high conversion also reflects this, averaging 1.3 at 120° C. and 2.0 at 180° C. It is believed these differences would have a significant effect on the melt-processing characteristics of the polymer, with the higher weight average molecular weight of the polymer produced at 180° C. expected to translate into better melt strength and processability.

These experiments show that polymerization at a higher temperature results in a polymer that is characteristically different. Further, the glass transition temperature for the samples polymerized at higher temperature is higher.

EXAMPLE 13

Experiments with Stabilizing Agents and Metal Deactivators

Test 1

Conditions: vial polymerization, (Lactide is melted under a nitrogen-purged atmosphere in a round bottom flask with stirring. Catalyst and additives are added and aliquots of the mixtures are pipetted into silanized glass vials. Typically 5–10 grams of reaction mixture are used in a 16 ml. vial. The vials are tightly capped and placed into a preheated oil bath.)

10,000:1 molar ratio of lactide-to-tin, tin(II) bis(2-ethyl hexanoate) catalyst, 0.2 wt percent Ultranox®626 in tetrahydrofuran (THF). 180° C. Time was 90 minutes.

The control with tin only polymerized to 84 percent conversion and reached a MWn of 31,700. The example with tin and Ultranox® polymerized to 83 percent conversion and reached a number average molecular weight (MWn) of 39,800; an increase of 26 percent over the control.

The control sample turned light yellow, the sample with stabilizer remained colorless.

Test 2

Conditions: vial polymerization, 5000:1 molar ratio of lactide to tin, tin(II) bis(2-ethyl hexanoate) catalyst, 0.25 wt percent Ultranox®626 (in THF). 180° C. Time was 60 minutes. Lactide was used from the above described Gruber et al. process.

The control with tin alone polymerized to 67 percent conversion and reached a MWn of 62,900. The example with tin and Ultranox® polymerized to 66 percent conversion and reached a MWn of 75800; an increase of 21 percent over the control.

A second example with tin(II) bis(2-ethyl hexanoate), Ultranox®, and 0.50 percent of Irganox® 1076, which is a phenolic antioxidant, polymerized to 66 percent conversion and reached a number average molecular weight (MWn) of 74500; an increase of 18 percent over the control.

All samples were a dark yellow color, although the samples with stabilizer had a slightly lower absorbance at 300 nm.

Test 3

Conditions: vial polymerization, 10,000:1 molar ratio of lactide to tin, tin(II) bis(2-ethyl hexanoate) catalyst, 180° C., 80 percent L-lactide and 20 percent D,L-lactide purchased from Henley and Aldrich, respectively. Lactic acid was added to control molecular weight to about 75,000 at full conversion. One sample included 0.25 percent Ultranox® 626 phosphite stabilizer, one included 0.25 percent Irganox® 1076 antioxidant, and one control sample.

Samples were taken at various times and analyzed by GPC for conversion and molecular weight (the method of Example 7). The results are summarized in Table 9 below.

TABLE 15

| Time | Control | | Irganox ® | | Ultranox ® | |
|---|---|---|---|---|---|---|
| (hrs) | Mn | % conv | Mn | % conv | Mn | % conv |
| 1 | 31,000 | 46 | 35,900 | 41 | 66,500 | 61 |
| 2 | 45,400 | 74 | 56,800 | 74 | 102,700 | 83 |
| 4 | 69,600 | 93 | 74,100 | 93 | 97,200 | 91 |
| 11 | 52,900 | 95 | 60.700 | 95 | 71,500 | 94 |

The sample with phosphite stabilizer polymerized faster, shown by the higher conversion at 1 and 2 hours, and went to a higher molecular weight than the control or the sample with Irganox®. The phosphite stabilized sample had a molecular weight more than 30 percent higher than the control for all time periods.

Test 4

The experiment above was repeated to compare the control to the phosphite-stabilized polymer, as summarized in Table 16 below.

TABLE 16

| Time | Control | | Ultranox ® | |
|---|---|---|---|---|
| (hrs) | Mn | % conv | Mn | % conv |
| 1 | 36,600 | 37 | 71,500 | 59 |
| 2 | 51,700 | 70 | 95,200 | 85 |
| 4 | 64,400 | 91 | 103,700 | 94 |
| 8 | 58,100 | 96 | 95,700 | 94 |

The sample with phosphite stabilizer again polymerized faster and went to a higher molecular weight than the nonstabilized sample. The phosphite stabilized sample had a molecular weight more than 60% higher than the control for all time periods.

Test 5

Conditions: vial polymerization, 5,000:1 molar ratio of lactide to tin, tin(II) bis(2-ethyl hexanoate) catalyst, 180° C., 80 percent L-lactide and 20 percent D,L-lactide purchased from Henley and Aldrich. Lactic acid was added to control number average molecular weight to an estimated 80,000 at full conversion. One sample was run with 0.25 percent Ultranox® 626 phosphite stabilizer, one with 0.25 percent Irganox® 1076 antioxidant, and one control sample.

Samples taken at various times and analyzed by GPC (the method of Example 1) for conversion and molecular weight. The results are tabulated in Table 17 below.

TABLE 17

| Time | Control | | Irganox ® | | Ultranox ® | |
|---|---|---|---|---|---|---|
| (hrs) | Mn | % conv | Mn | % conv | Mn | % conv |
| 1 | 83,600 | 76 | 121,900 | 83 | 162,300 | 87 |
| 4 | 74,400 | 93 | 104,300 | 95 | 123,900 | 96 |
| 24 | 40,200 | 96 | 52,000 | 96 | 96,900 | 97 |
| 48 | 34,200 | 97 | 30,400 | 96 | 56,500 | 96 |
| 72 | 25,000 | 96 | 22,400 | 96 | 69,500 | 96 |

The phosphite-stabilized sample had a molecular weight more than 60 percent higher than the control for all time periods. After 72 hours it had a molecular weight 2.8 times higher than the control. The sample with antioxidant showed an initial increase in molecular weight, relative to the control, but the effect disappeared after 48 hours.

The phosphite stabilized sample was significantly lighter in color than the control or the antioxidant treated sample.

Test 6

Conditions: vial polymerization, 5000:1 molar ratio of lactide to tin, tin(II) bis(2-ethyl hexanoate) catalyst, 0.25 wt percent Ultranox® 626 (in THF). 180° C. Time was two hours. Gruber et al. process lactide washed with isopropyl alcohol was used.

The control with tin alone polymerized to 95 percent conversion and reached a number average molecular weight of 118,000. The example with tin and Ultranox® polymerized to 93 percent conversion and reached a number average molecular weight of 151,000, an increase of 28 percent over the control.

Test 7

Conditions: vial polymerization at 180° C. 5000:1 molar ratio of lactide to tin, tin(II) bis(2-ethyl hexanoate) catalyst. Lactide was 80 percent L-lactide and 20 percent D,L-lactide, purchased from Henley and from Aldrich. Lactic acid was added to target the molecular weight to an Mn of 80,000. All stabilizers were added at 0.25 weight percent. Molecular weight (number average) was determined for samples pulled at 3 hours, while rate constants were based on samples pulled at 1 hour. The results of these screening tests on many stabilizing agents following the above procedure are detailed below in Table 18. Product designations in Table 18 are tradenames or registered trademarks.

TABLE 18

| Sample | | MWn | % Conversion | Relative Rate |
|---|---|---|---|---|
| Control 1 | | 65,000 | 95.9 | 90 |
| Control 2 | | 85,000 | 95.9 | 100 |
| Control 3 | | 76,000 | 96.6 | 100 |
| Control 4 | | 69,000 | 96.2 | 100 |
| Control 5 | | 74,000 | 96.8 | 110 |
| Control 6 | | 70,000 | 97.2 | 110 |
| PHOSPHITES | | | | |
| Ultranox 626 | (GE) | 103,000 | 96.8 | 100 |
| Weston TDP | (GE) | 64,000 | 70.0 | 60 |
| Weston PDDP | (GE) | 67,000 | 76.7 | 60 |
| Weston PNPG | (GE) | 92,000 | 94.1 | 100 |
| Irgafos 168 | (Ciba-Geigy) | 95,000 | 95.3 | 120 |
| Weston 618 | (GE) | 99,000 | 95.1 | 100 |
| Sandostab P-EPQ | (Sandoz) | 108,000 | 94.7 | 110 |
| Weston TNPP | (GE) | 88,000 | 97.9 | 130 |
| PHENOLIC ANTIOXIDANTS | | | | |
| Irganox 1010 | (Ciba-Geigy) | 95,000 | 97.5 | 110 |
| Cyanox 1790 | (Cyanamid) | 98,000 | 96.9 | 120 |
| BHT | | 87,000 | 96.5 | 130 |
| Irganox 1076 | (Ciba-Geigy) | 121,000 | 97.8 | 130 |
| Topanol CA | (ICI) | 84,000 | 96.6 | 160 |
| AMINES | | | | |
| Tinuvin 123 | (Ciba-Geigy) | 65,000 | 94.8 | 70 |
| Tinuvin 622 | (Ciba-Geigy) | 82,000 | 95.7 | 80 |
| Naugard 445 | (Uniroyal) | 93,000 | 98.2 | 120 |
| THIOETHER | | | | |
| Mark 2140 | (Witco) | 77,000 | 97.0 | 120 |
| METAL DEACTIVATORS | | | | |
| Irganox MD1024 | (Ciba-Geigy) | 34,000 | 65.7 | 10 |
| Naugard XL-1 | (Uniroyal) | 91,000 | 95.8 | 110 |

Note, that with a few exceptions, the phosphites and the phenolic antioxidants provide increased molecular weight with no reduction in polymerization rate. Of the amines, only Naugard® 445 provided stabilization without a rate decrease. The metal deactivators are expected to deactivate the catalyst, as was observed for Irganox® MD1024. The Naugard® XL-1 did not accomplish deactivation.

EXAMPLE 14

Polymer Melt Stability as a Function of Moisture Content

Lactide, produced and purified in a continuous (Gruber et al.) process, was fed at a rate of 3 kg/hr to a continuous polymerization pilot plant. Catalyst was added with a metering pump at the rate of 1 part catalyst to 5000 parts lactide on a molar basis. The reaction system was blanketed with nitrogen. The reactor vessels consist of two continuous stirred tank reactors (CSTR) in series. The first had a 1-gallon capacity and the second had a 5-gallon capacity. The reactors were run 60–80 percent liquid filled and at 170°–180° C. Polymer melt pumps moved the liquid from CSTR 1 to CSTR 2, and from CSTR 2 through a die into a cooling water trough. The polymer strand thus produced was pulled from the trough by a pelletizer and stored as pellets.

The pelletized poly(lactide) was put into a drying hopper and dried at 40° C. under flowing dry air. Samples were pulled after one hour and four hours. These samples were then run through a single screw Brabender® extruder, with a retention time of approximately 3 minutes. Samples were analyzed for moisture by an automatic Karl Fischer apparatus and for molecular weight by GPC (the method of Example 7). The results of these tests are documented in Table 19 below.

TABLE 19

| Sample | Extruder Temperature (C.) | Weight Average Molecular Weight |
|---|---|---|
| Initial | | 63,000 |
| Dried 1 hour | 137 | 44,000 |
| (1200 ppm H$_2$O) | 145 | 48,000 |
| | 162 | 35,000 |
| | 179 | 30,000 |
| Dried 4 hours | 140 | 63,000 |
| (150 ppm H$_2$O) | 140 | 69,000 |
| | 160 | 65,000 |
| | 178 | 68,000 |

These results show the detrimental effect of water in the lactide polymer resin during melt polymerization and the need to properly dry the poly(lactide) before melt-processing.

EXAMPLE 15

Degradation of Crystalline and Amorphous Poly(lactide)

Two literature references disclose poly(D,L- lactide) to degrade faster than poly(L-lactide), attributing the result to crystallinity of poly(L-lactide). These are: Kulkarni et al., *J. Biomed. Mater. Res.*, vol. 5, pp. 169–181, (1971); Makino et al., *Chem. Pharm. Bull.*, vol. 33, pp. 1195–1201, (1985). An experiment was conducted to measure the effect of crystallinity on polymer degradation and is detailed below.

An amorphous poly(lactide) sample (clear, and less than 1 percent crystallinity based on DSC) and a crystalline poly(lactide) sample (opaque, and approximately 50 percent crystallinity based on DSC) were subjected to biodegradation in a compost test (50° C., with aeration). The DSC apparatus was a TA Instruments, Inc., model 910 differential scanning calorimeter with DuPont 9900 computer support system typically programmed to heating at a rate of 10° C. per minute to 200° C. The samples had different optical composition, with the crystalline sample being more than 90 percent poly(L-lactide) and the amorphous sample being less than 80 percent poly(L-lactide) with the balance being either poly(D,L-lactide) or poly(meso-lactide). Samples of each polymer were subjected to a compost test (ASTM D 5338) which included mixing a stabilized compost and providing a source of humidified air while maintaining a temperature of about 50° C. The amorphous sample was completely degraded after 30 days of composting. The crystalline sample was only 23 percent degraded based on carbon dioxide after the same period of time.

Additional samples of these two polymers were subjected to chemical hydrolysis at 50° C. (hydrolysis is believed to be the rate-limiting step in the biodegradation process). The chemical hydrolysis procedure included placing 0.1 gram poly(lactide) in 100 ml of 0.2M phosphate buffer (pH=7.4). The samples were held for 1 week, then filtered, washed with deionized water, and dried at 25° C. under vacuum. The initial weight average molecular weight for each sample was about 70,000. After 1 week the amorphous sample had a weight average molecular weight of 10,000 and the crystalline sample had a weight average molecular weight of 45,000, determined by GPC (the method of Example 7). Neither sample had significant weight loss at this time.

Both of these tests demonstrate that degradation of crystalline poly(lactide) is slower than degradation of amorphous poly(lactide).

EXAMPLE 16

Effect of Monomer Concentration on Film Modulus

Poly(lactide) was precipitated in methanol from a chloroform solution in order to remove the residual lactide monomer. GPC analysis (the method of Example 1) showed the precipitated polymer to contain 0.0 percent lactide.

The polymer was dissolved in chloroform to make a 10 wt percent solution, and lactide was added back to make 5 separate solutions which, after removing the chloroform, are calculated to produce films containing 0.0, 0.2, 0.4, 1.0 and 4.0 weight percent lactide in poly(lactide). These solutions were solvent cast onto glass, dried overnight at room temperature in a fume hood, and removed to a vacuum oven. The films were hung in the vacuum oven and dried at 30° C. for 72 hours. GPC analysis of the vacuum-dried films showed measured lactide levels of 0.0, 0.0, 0.4, 0.7 and 3.7 wt percent.

The films were then tested for film modulus using ASTM procedure D882.

The results are shown below in Table 20.

TABLE 20

| % Lactide | Tensile (psi avg.) | Std. Dev. | % Elongation | Std. Dev. | Elastic Modulus (psi avg.) | Std. Dev. |
|---|---|---|---|---|---|---|
| 0 | 5490 | 636 | 2.85 | 0.14 | 730,000 | 103,000 |
| 0 | 6070 | 123 | 2.85 | 0.22 | 818,000 | 35,000 |
| 0.4 | 5670 | 227 | 2.75 | 0.27 | 779,000 | 44,000 |
| 0.7 | 5690 | 343 | 4.04 | 1.12 | 749,000 | 58,000 |
| 3.7 | 5570 | 458 | 3.33 | 1.43 | 738,000 | 66,000 |

EXAMPLE 17

Rate of Water Uptake Versus Optical Composition

Samples of poly(lactide), made from 80 percent L-lactide and 20 percent of either D,L-lactide or meso-lactide, were ground to pass a 20 mesh screen. The samples were dried and devolatilized under vacuum then removed to a constant humidity chamber maintained at 24° C. and 50 percent relative humidity. The rate of moisture pick-up was determined gravimetrically, with the final results verified by Karl-Fischer water analysis. The rate of moisture pickup is shown below in Table 21.

TABLE 21

| Time (Minutes) | Parts Per Million Weight Gain | |
|---|---|---|
| | L/D,L Polymer | L/Meso Polymer |
| 10 | 600 | 1000 |
| 30 | 1100 | 1500 |
| 60 | 1500 | 1800 |
| 120 | 1600 | 2100 |
| 870 | 2100 | 2600 |
| Final (Karl-Fischer) | 3000 | 2600 |

EXAMPLE 18

Standard Test of Melt Stability

A standard test for determining melt stability is as follows:

A small sample (200 grams or less) of polymer is ground or pelletized and devolatilized by holding under vacuum (about 10 mm Hg) at a temperature of 130° C. or less for 18 hours. At this point the residual lactide content should be 1 wt percent or less. Portions (1–5 grams) of the devolatilized sample are then placed in a 16 ml sample vial, tightly capped, and placed in a 180° C. oil bath. Samples are removed at times of 15 minutes and 1 hour and analyzed for lactide content by GPC or other appropriate techniques. Lactide which may collect on the cooler portions of the vial is included in the product work-up and test.

Melt-stabilized poly(lactide)s will maintain lactide contents of less than 1 percent in both the 15 minute and 1 hour samples, preferably less than 0.5 percent. An unstabilized poly(lactide) may reach the equilibrium lactide content at 180° C. of 3.6 wt percent, or may go even higher as lactide is driven from the polymer melt and collects on the cooler top walls of the vial.

EXAMPLE 19

Water Scavenger Experiments

Dried poly(lactide) pellets were processed in a twin screw extruder to devolatilize and to prepare a portion with 0.5 percent by weight of a water scavenger (Stabaxol® P). The strands leaving the extruder are cooled in a water trough and chopped into pellets. Samples of the control and the test sample were then analyzed by the Karl Fischer technique for moisture content, with no drying. The control sample contained 1700 ppm water, the test sample had 450 ppm water. The control sample was then dried under nitrogen at 40° C., reducing the water content to 306 ppm. A vacuum-dried control sample had 700 ppm water.

The as-produced test sample and the dried control samples were then processed in a ½" single screw extruder (Brabender®) at 160° C., with a retention time of 3 minutes. The number average molecular weight for the dried control sample dropped from an initial value of 44,000 to a final value of 33,000 for the 306 ppm water sample and to 28,000 for the 700 ppm water sample. The test sample number average molecular weight dropped from an initial value of 40,000 to a final value of 33,000.

This sample shows how the water scavenger protected the polymer from moisture pick-up, imparting the same stability as a thorough drying of the control sample. Combining a water scavenger with appropriate drying is expected to give even greater stability.

EXAMPLE 20

Optimization of Catalyst Concentration

A mixture of 80 percent L-lactide and 20 percent D,L-lactide was polymerized using three different levels of tin(II) bis(2-ethyl hexanoate) catalyst. Batches were prepared at initial monomer/catalyst molar ratios of 1000:1, 3000:1, and 20,000:1. Polymerization times were adjusted to reach high conversion without being excessively long and thereby causing degradation in the melt. The reaction times were 1, 2 and 20 hours, respectively. The polymerization temperature was 180° C. The polymers were ground to a coarse powder and devolatilized at 125° C. and 10 mm Hg overnight. The samples were then reground and 1-gram portions of each were placed into silanized vials, 16 ml capacity. The vials were sealed and placed into an oil bath at 180° C. Vials were then removed at various times and the samples were analyzed by GPC after dissolution in chloroform. The molecular weights and lactide contents are shown below in Table 22.

TABLE 22

| Sample | Time (min) | Number Average Molecular Weight | Weight Average Molecular Weight | Lactide Weight % |
|---|---|---|---|---|
| 1000:1 | 0 | 39,000 | 81,300 | 0.8 |
| | 5 | 28,100 | 57,300 | 2.4 |
| | 15 | 25,800 | 49,700 | 2.8 |
| | 30 | 23,100 | 43,800 | 3.7 |
| | 60 | 22,800 | 43,200 | 3.6 |
| 3000:1 | 0 | 53.100 | 113,600 | 0.6 |
| | 5 | 39,000 | 76,400 | 0.4 |
| | 15 | 30,300 | 65,400 | 1.9 |
| | 30 | 29,000 | 60,400 | 2.7 |
| | 60 | 28,200 | 55,200 | 2.8 |
| 20000:1 | 0 | 89,200 | 184,000 | 0.0 |
| | 5 | 81,200 | 165,100 | 0.0 |
| | 15 | 54,300 | 134.600 | 0.1 |
| | 30 | 51,100 | 119,600 | 0.0 |
| | 60 | 49,500 | 111,000 | 0.0 |

These results show the benefit of optimizing the catalyst level used in the polymerization process. Note that both lactide reformation and molecular weight retention benefits are realized from the reduced catalyst levels (higher monomer/catalyst ratio).

It is believed catalyst levels should be limited to 1000:1 for the high end of catalyst usage, with 3000:1 being more preferable and showing somewhat improved stability. Lower levels still, such as 20000:1, show greatly improved stability. Beyond this level it is believed the polymerization rates become too slow to be practical.

EXAMPLE 21

Removal of Tin Catalyst from Poly(lactide) by Precipitation 45 grams of L-lactide and 13 grams of D,L-lactide were charged with 78 milligrams of crystalline lactic acid to a 200 ml round bottom flask. This was heated to 180° C. with magnetic stirring in an oil bath and blanketed with dry nitrogen. Catalyst in the form of tin(II) bis(2-ethyl hexanoate) was added as 0.20 ml of a 0.47 g/ml solution in THF after the molten lactide was at temperature. The mixture was allowed to stir for one minute and then pipetted into 3 silanized glass vials, which were then sealed and placed into a 180° C. oil bath for 75 minutes. The vials were allowed to cool and the polymer recovered by breaking the glass. The polymer was ground to a coarse powder and dissolved in chloroform to make a 10 percent solution. The polymer contained 3.8 percent residual monomer and had a number average molecular weight of 70,000 as determined by GPC measurement (the method of Example 7).

500 ml of methanol were placed in a 1-liter glass blender flask. The blender was turned on to medium speed and 50 ml of the polymer in chloroform solution was poured in over a period of three minutes. After one additional minute of blending the mixture was filtered, then rinsed with 100 ml of methanol, and dried overnight under vacuum. The polymer consisted of a fibrous mat. It contained 0.3 percent residual monomer and had a number average molecular weight of 66,900.

The measured tin level in the precipitated polymer was 337 ppm by weight, compared to a calculated value of 466 ppm for the as-produced polymer. This result indicates the feasibility of reducing residual catalyst levels in lactide polymers by solvent precipitation with the benefit of improved stability as detailed in Example 20.

EXAMPLE 22

Shear Rate

Samples of devolatilized poly(lactide) were tested in a Rosand Model 14° C. capillary rheometer. The die was 1 mm diameter and 16 mm long, with an entry angle of 180 degrees. The table below gives the pressure drop across the die as a function of nominal shear rate (not Rabinowitsch corrected) for various molecular weights and temperatures.

TABLE 23

| Mn | MW | Temp (°C.) | Nominal shear rate ($s^{-1}$) | Pressure Drop (MPa) |
|---|---|---|---|---|
| Results at 150° C. | | | | |
| 34,000 | 70,000 | 150 | 192 | 2.0 |
| | | | 384 | 5.5 |
| | | | 960 | 10.0 |
| | | | 1920 | 13.8 |
| | | | 4800 | 19.7 |
| | | | 9600 | 23.7 |
| 52,000 | 108,000 | 150 | 192 | 9.9 |
| | | | 384 | 15.6 |
| | | | 960 | 19.9 |
| | | | 1920 | 23.9 |
| | | | 4800 | 29.4 |
| | | | 9600 | — |
| 60,000 | 137,000 | 150 | 192 | 7.4 |
| | | | 384 | 11.1 |
| | | | 960 | 16.6 |
| | | | 1920 | 21.0 |
| | | | 4800 | — |
| | | | 9600 | — |
| 183,000 | 475,000 | 150 | 192 | 19.1 |
| | | | 384 | 27.0 |
| | | | 960 | 31.4 |
| | | | 1920 | — |
| | | | 4800 | — |
| | | | 9600 | — |
| Results at 175° C. | | | | |
| 34,000 | 70,000 | 175 | 192 | 0.4 |
| | | | 384 | 0.5 |
| | | | 960 | 3.4 |
| | | | 1920 | 5.5 |

TABLE 23-continued

| Mn | MW | Temp (°C.) | Nominal shear rate (s$^{-1}$) | Pressure Drop (MPa) |
|---|---|---|---|---|
| | | | 4800 | 9.2 |
| | | | 9600 | 12.5 |
| 52,000 | 108,000 | 175 | 192 | 2.2 |
| | | | 384 | 4.6 |
| | | | 960 | 7.6 |
| | | | 1920 | 11.5 |
| | | | 4800 | 17.2 |
| | | | 9600 | 22.1 |
| 183,000 | 475,000 | 175 | 192 | 11.5 |
| | | | 384 | 16.6 |
| | | | 960 | 20.2 |
| | | | 1920 | 24.4 |
| | | | 4800 | 29.9 |
| | | | 9600 | — |
| Results at 200° C. | | | | |
| 60,000 | 137,000 | 200 | 192 | 0.5 |
| | | | 384 | 1.6 |
| | | | 960 | 3.3 |
| | | | 1920 | 5.3 |
| | | | 4800 | — |
| | | | 9600 | 13.2 |
| 183,000 | 475,000 | 200 | 192 | 7.0 |
| | | | 384 | 11.0 |
| | | | 960 | 14.2 |
| | | | 1920 | 17.9 |
| | | | 4800 | 21.6 |
| | | | 9600 | — |

EXAMPLE 23

Process Stabilizer Effect on Rate of Hydrolysis

Poly(lactide) was produced using a vial polymerization of lactide at 180° C. for 2 hours. The catalyst (tin(II) bis(2-ethyl hexanoate)) was used in a molar ratio of 1 part catalyst to 10,000 parts lactide. One of the samples had 0.25 wt-% of the process stabilizer PNPG (commercially available from General Electric) added to the molten lactide.

Hydrolysis was carried out in 0.2M phosphate buffer (pH 7.4) at 75° C. Results with and without the stabilizer are shown in the table below:

TABLE 23(a)

| | Weight Average Mol. Wt. | | Weight % Remaining | |
|---|---|---|---|---|
| Day | With PNPG | Without | With PNPG | Without |
| 0 | 127,000 | 116,000 | 100 | 100 |
| 1 | 23,700 | 24,500 | 84 | 82 |
| 2 | 4,600 | 10,700 | 70 | 74 |
| 3 | 12,600 | 6,000 | 63 | 64 |
| 4 | 5,700 | 4,800 | 74 | 68 |
| 5 | 4,500 | 3,800 | 75 | 79 |
| 7 | 3,800 | 4,600 | 42 | 62 |

The results show that the process stabilizer had no effect on the rate of hydrolysis.

EXAMPLE 24

The Effect of Meso-lactide Concentration on Crystallization

Samples of devolatilized poly(lactide) of varying optical composition and with number average molecular weights in the range of 50,000 to 130,000 were prepared in a continuous pilot plant. The samples were dissolved in chloroform to a concentration of 5 grams/100 cc and the optical rotation of the samples was measured to determine the concentration of meso-lactide which had been present in the monomer mixture prior to polymerization. Separate optical rotation and gas chromatography analysis of the monomer mixture confirmed that L-lactide and meso-lactide are the predominate components when meso-lactide is present at a concentration of 20 percent or less, and only a small correction is required for D-lactide.

Additional samples were made by polymerizing mixtures with known weights of L-lactide and meso-lactide.

All samples were subjected to an annealing procedure to develop crystallinity. The annealing procedure consisted of placing the samples in an oven at 100°–105° C. for 90 minutes, then lowering the temperature 10° C. each ½ hour until the temperature reached 45° C. The oven was then shut off and the samples were allowed to cool to room temperature. The energy of the melting endotherm and the peak melting temperature were then measured using a Mettler Differential Scanning Calorimeter (DSC) apparatus with a scan speed of 20° C./minute. The energy of melting is a measure of crystallinity in the annealed samples.

Figure 3:
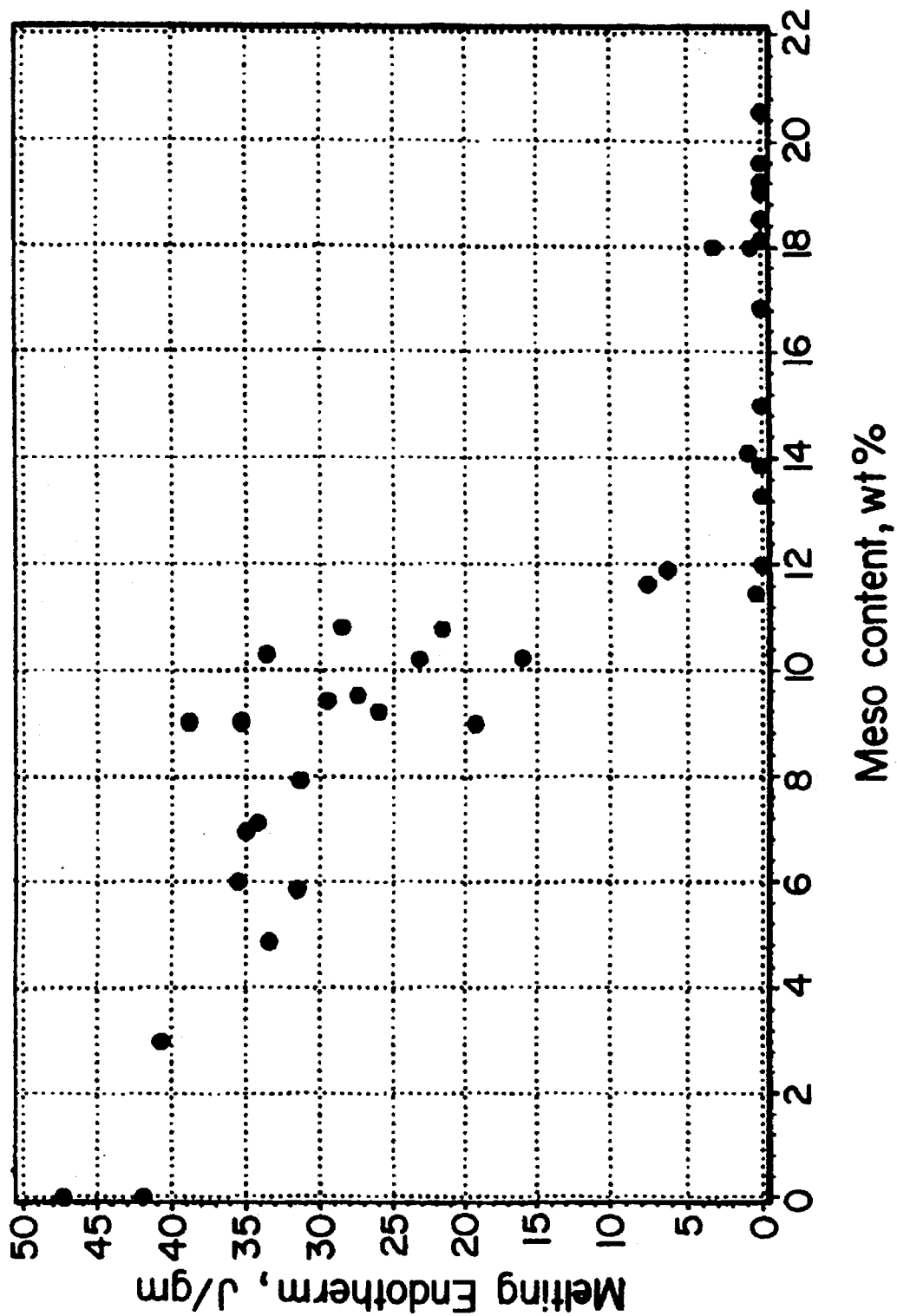
FIG. 3 is a graph showing the melting endotherm for annealed samples of poly(lactide).

FIG. 3 shows the sharp decline in crystallinity between 9 and 12 percent meso content.

EXAMPLE 25

Properties of Poly(lactide) Cellulose Acetate Blends

In the twin screw extruder described in Example 3, PLA was blended with cellulose acetate (Tenite 110 from Eastman), cellulose acetate propionate (Tenite 375 from Eastman), and cellulose butyrate (Tenite 575 from Eastman) in levels shown in the table. The poly(lactide) had a weight average molecular weight of about 200,000, a meso content of about 10.5%, a residual lactide level of about 0.3%, and a moisture content less than about 300 ppm. The weight percentages of poly(lactide) and cellulose derivatives are shown in the following table:

TABLE 24

| Composition | 1 | 2 | 3 | 4 | 5 | 6 | 7 | 8 | 9 | 10 |
|---|---|---|---|---|---|---|---|---|---|---|
| CA | | 20% | 50% | 80% | | | | | | |
| CAP | | | | | 20% | 50% | 80% | | | |
| CAB | | | | | | | | 20% | 50% | 80% |
| PLA | 100% | 80% | 50% | 20% | 80% | 50% | 20% | 80% | 50% | 20% |

The blends were prepared using a melt temperature of 190°–200° C., die pressure of 18–20 bar, and a screw speed of 250 rpm. All materials but one were pelletized, dried and injection molded into a standard ASTM test specimen mold for testing. Composition 3 was not pelletized due to poor strength of the extruded polymer stand. This is evidence of mechanical incompatibility of the cellulose acetate and poly(lactide). The remaining compositions were tested for tensile strength and elongation to break in accord with ASTM D 638-91 and heat distortion temperature according to ASTM D 648-82.

Another test performed on each sample was a teste for resistance to hot water. A standard tensile bar is placed in a hot water bath at 190° F. for 3 minutes. The sample is removed from the water and placed in a horizontal position with the flat sides facing up and down with one end of the tensile bar held in a clamp. Samples which have softened as a result of the hot water exposure will bend under the force of gravity. The degree of bend is measured using a protractor. The maximum degree of bend is 90° and constitutes a failure. The best result is no bend of the sample.

The test results are shown in the following table:

TABLE 25

| Sample | Tensile strength to break (psi) | Elongation to break (%) | Heat distortion temperature (°C.) | Hot water test angle of (deformation) |
|---|---|---|---|---|
| 1 | 7100 | 5.4 | 51.1 | 46° |
| 2 | 5900 | 1.5 | 41.7 | 44° |
| 3 | — | — | — | — |
| 4 | 3200 | 2.2 | — | 0° |
| 5 | 8100 | 2.2 | 46.7 | 10° |
| 6 | 5600 | 6.9 | 45.7 | 3° |
| 7 | 4700 | 17.9 | 50.0 | 0° |
| 8 | 7600 | 2.3 | 48.2 | 23° |
| 9 | 5500 | 8.3 | — | 0° |
| 10 | 5100 | 17.9 | 51.9 | 0° |

These results show that many compositions of poly(lactide) blended with CA, CAP and CAB are compatible enough to exhibit good physical properties. Blends of PLA with high loadings of CAP and CAB may increase the flexibility of unblended poly(lactide). Resistance of poly(lactide) to hot water was dramatically increased by addition of CA, CAP or CAB.

EXAMPLE 26

Effect of Optical Composition on Hydrolysis Rate

Poly(lactide) samples of various optical composition were prepared by melting, under nitrogen, the lactide monomers and adding catalyst to the molten monomer. Catalyst (tin (II) bis 2-ethyl hexanoate) was added on a molar basis in the ratio of 1 part catalyst to 500 pars lactide. The mixture was placed in a sealed vial and polymerized in a hot oil bath at a temperature of 180° C. for 2 hours. Conversion to polymer was 92% or higher.

The hydrolysis test consists of placing 0.1 gram of polymer pellets into 100 ml of a 0.2 phosphate buffer solution with pH=7.4. The solution is maintained at 75° C. through the test. A series of samples are made up and pulled at various times throughout the test. The contents are collected on a #2 Whatman filter, washed with deionized water, and dried at 25° C. under vacuum.

The table below shows the weight average molecular weight (determined by GPC in chloroform at 35° C., calibrated against polystyrene standards) and the percent residue remaining from samples made from 100% L-lactide, 100% D,L-lactide, and 100% meso-lactide. Each of the samples was initially amorphous. The sample made from L-lactide showed potential crystallinity of 47 J/gm when subjected to the standard annealing procedure of Example 24. The samples made from D,L-lactide and from meso-lactide showed endotherms of 1.2 and 0 J/gm after annealing, respectively, thus indicating non-crystallizing samples.

TABLE 27

| | Weight Average Mol. Wt. | | | Weight % Remaining | | |
|---|---|---|---|---|---|---|
| Day | L | D,L | meso | L | D,L | meso |
| 0 | 44,600 | 36,800 | 42,400 | 100 | 100 | 100 |
| 1 | 38,800 | 14,700 | 11,900 | 76 | 77 | 81 |
| 2 | 20,000 | 8,100 | 7,200 | 69 | 43 | 24 |
| 3 | 11,000 | 5,400 | 5,000 | 73 | 12 | 3 |
| 4 | 16,500 | 4,300 | 5,000 | 84 | 14 | 9 |
| 5 | 7,300 | 4,300 | 5.000 | 82 | 19 | 10 |
| 7 | 7,000 | 4,300 | 5,000 | 74 | 7 | 7 |

The results show that poly(lactide) made from pure L-lactide hydrolyzes much slower than does poly(lactide) made from either D,L-lactide or meso-lactide. This is believed to be due to crystallization of the poly(L-lactide) during the hydrolysis test.

EXAMPLE 27

Effect of Annealing on Hydrolysis of Samples with the Same Optical Composition

Poly(lactide) pellets, produced in a continuous pilot plant and then dried, devolatilized, and dried again, were subjected to the hydrolysis test of Example 26. The optical composition of the lactide in the pilot plant is estimated to be about 90 wt % L-lactide and about 10 wt-% meso-lactide. One of the samples was subjected to the standard annealing process prior to the hydrolysis procedure, developing 37 J/gm of crystallinity. The second sample was not annealed, and was initially amorphous. (less than 1 J/gm) The table below shows the hydrolysis results for the two samples as a function of time.

TABLE 28

| | Weight Average Mol. Wt. | | Weight % Remaining | |
|---|---|---|---|---|
| Day | Annealed | Not annealed | Annealed | Not annealed |
| 0 | 103,000 | 106,700 | 100 | 100 |
| 2 | 38,900 | 20,900 | 84 | 81 |
| 3 | 15,500 | 12,400 | 58 | 52 |
| 6 | 12,700 | 10,000 | 55 | 38 |
| 30 | 11,900 | 11,000 | 33 | 30 |
| 60 | 9,200 | 9,000 | 25 | 23 |
| 90 | 9,200 | 9,000 | 10 | 9 |
| 120 | 9,200 | 9,000 | 0 | 0 |

The results show that both the annealed sample and the amorphous sample hydrolyzed at the same rate. This is believed to be due to crystallization of the initially amorphous sample during the hydrolysis test.

EXAMPLE 28

Demonstration of Crystallization during Hydrolysis

Poly(lactide) was dried, devolatilized, redried, and compounded with 15% talc and 2% $TiO_2$. The lactide used to make the polymer was predominately L-lactide, with about 11% meso-lactide. The pellets were dried again and cast into a sheet suitable for thermoforming. Samples of two thermoformed articles were then subjected to a hydrolysis test in 0.2M phosphate buffer. The temperature of the solution was adjusted following the ASTM compost profile (ASTM D 5338), consisting of day 1 at 35° C., days 2–5 at 58° C., days 6–27 at 50° C., and days 28–45 at 35° C. The results of the test are shown below:

TABLE 29

|     | Weight Average Mol. Wt. | | Crystallinity (J/gm) | |
| --- | --- | --- | --- | --- |
| Day | Article 1 | Article 2 | Article 1 | Article 2 |
| 0   | 230,400 | 231,200 | 0.0  | 0.0  |
| 7   | 97,400  | 90,700  | 16.9 | 17.5 |
| 14  | 67,700  | 69,800  | 18.7 | 22.8 |
| 21  | 45,800  | 33,100  | 26.9 | 23.2 |
| 28  | 17,700  | 15,900  | 26.9 | 23.2 |

The results show the development of crystallinity in an initially amorphous article during the hydrolysis test.

It will be understood that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed:

1. A film having a net endotherm of less than about 10 joules per gram of polymer containing chains including lactic acid residuals; said film further comprising:
   (a) a melt-stable polymer composition including at least 5% by weight of a melt-stable first polymer component including polymer chains containing lactic acid residuals, based on total weight of melt-stable polymer in said melt-stable polymer composition;
      (i) said first polymer component being formed from at least:
         (A) a source of (R)-lactic acid residuals; and,
         (B) a source of (S)-lactic acid residuals;
      (ii) said first polymer component having (R)-lactic acid residuals and (S)-lactic acid residuals in a distribution in the polymer such that sequences of a major lactic acid residual have at least a 0.5 probability of including a sequence of less than 10 of the major lactic acid residuals consecutively;
   (b) said first polymer component having a number average molecular weight of at least 40,000 and no greater than about 300,000; and,
   (c) said melt stable polymer composition having a lactide concentration, if present at all, of less than about 2% by weight of melt-stable polymer in said first polymer component;
   (d) said melt-stable first polymer component being a material in a form sufficiently melt stable such that a devolatilized sample of it, when isolated and prior to formation of said melt-stable polymer composition, will show formation of less than 1% lactide presence, by weight, after heating for 1 hour at 180° C.

2. A film according to claim 1 wherein:
   (a) said source of (R)-lactic acid residuals from which said first polymer component is formed includes meso-lactide; and
   (b) said source of (S)-lactic residuals from which said first polymer component is formed also includes meso-lactide and further includes L-lactide.

3. A film according to claim 2 wherein:
   (a) said source of (R)-lactic acid residuals further includes D-lactide.

4. A film according to claim 2 wherein:
   (a) said first polymer component comprises a plurality of polymer chains having at least meso-lactide residuals and L-lactide residuals; said plurality of polymer chains being formed from a lactide mixture comprising greater than about 1% by weight meso-lactide, based on a total weight of meso-lactide, L-lactide and any D-lactide present.

5. A film according to claim 4 wherein:
   (a) said first polymer component comprises polymer chains which are structurally modified from poly(lactide).

6. A film according to claim 5 wherein:
   (a) said melt stable first polymer component is formed from material containing epoxidized oil.

7. A film according to claim 5 wherein:
   (a) said first polymer component includes an epoxide material reacted into the polymer chains.

8. A film according to claim 5 wherein:
   (a) said first polymer component comprises a polymer formed from at least: meso-lactide, L-lactide and a molecular weight control agent.

9. A film according to claim 8 wherein:
   (a) said molecular weight control agent comprises a chain initiator having more than one reactive group for initiating lactide polymerization.

10. A film according to claim 8 wherein:
    (a) said molecular weight control agent is selected from the group consisting of: diols, triols and glycols.

11. A film according to claim 5 wherein:
    (a) said first polymer component comprises a polymer formed from: meso-lactide, L-lactide and at least one other material capable of reacting into the polymer.

12. A film according to claim 11 wherein:
    (a) said at least one other material capable of reacting into the polymer includes D-lactide.

13. A film according to claim 12 wherein:
    (a) said at least one other material capable of reacting into the polymer includes a chain-initiating agent selected from the group consisting essentially of: lactic acid, esters of lactic acid, alcohols, amines, glycols, diols, and triols.

14. A film according to claim 11 wherein:
    (a) said at least one other material capable of reacting into the polymer includes a material having more than one functional group capable of reacting into the polymer chains.

15. A film according to claim 14 wherein:
    (a) said material having more than one functional group capable of reacting into the polymer chains is selected from the group consisting essentially of: diols, triols and glycols.

16. A film according to claim 4 wherein:
    (a) said melt stable first polymer component is formed from material containing epoxidized oil.

17. A film according to claim 4 wherein:
    (a) said first polymer component includes an epoxide material reacted into the polymer chains.

18. A film according to claim 1 further comprising:
(a) a polymer blend of said first polymer component with a second polymer component;
   (i) said second polymer component comprising a polymer that does not contain lactic acid residuals therein.

19. A film according to claim 1 wherein:
(a) said melt stable polymer composition has a water concentration, if water is present at all, of less than about 500 parts per million.

20. A film according to claim 1 wherein:
(a) said first polymer component comprises a poly(lactide) copolymer.

21. A film having a net endotherm of less than about 10 joules per gram of polymer containing chains including lactic acid residuals; said film further comprising:
(a) a melt-stable polymer composition including at least 5% by weight of a melt-stable first polymer component including polymer chains containing lactic acid residuals, based on total weight of melt-stable polymer in said melt-stable polymer composition;
   (i) said first polymer component comprising polymer chains comprising at least 50% by weight residues selected from the group consisting essentially of L-lactide, D-lactide, and mixtures thereof; and,
   (ii) said first polymer component having (R)-lactic acid residuals and (S)-lactic acid residuals in a distribution in the polymer such that sequences of a major lactic acid residual have at least a 0.5 probability of including a sequence of less than 10 of the major lactic acid residuals consecutively;
(b) said first polymer component having a number average molecular weight of at least 40,000 and no greater than about 300,000; and,
(c) said melt stable polymer composition having a lactide concentration, if present at all, of less than about 2% by weight of melt-stable polymer in said first polymer component;
(d) said melt-stable first polymer component being a material in a form sufficiently melt stable such that a devolatilized sample of it, when isolated and prior to formation of said melt-stable polymer composition, will show formation of less than 1% lactide presence, by weight, after heating for 1 hour at 180° C.

22. A film according to claim 21, wherein:
(a) the first polymer component being formed from a reactant mixture comprising greater than about 9% by weight meso-lactide.

23. A film according to claim 22 wherein:
(a) said melt stable first polymer component is formed from material containing epoxidized oil.

24. A film according to claim 21 wherein:
(a) said melt stable first polymer component is formed from material containing epoxidized oil.

25. A film according to claim 21 wherein:
(a) said first polymer component includes an epoxide material reacted into the polymer chains.

26. A film according to claim 21 wherein:
(a) said molecular weight control agent comprises a chain initiator having more than one reactive group for initiating lactide polymerization.

27. A film according to claim 8 wherein:
(a) said molecular weight control agent is selected from the group consisting of: diols, triols and glycols.

28. A process of preparing a film having a net endotherm of less than about 10 joules per gram of polymer containing lactide residuals; said process including a step of:
(a) extruding a melt-stable polymer composition including at least 5% by weight of a melt-stable first polymer component including polymer chains containing lactic acid residuals, based on total weight of melt-stable polymer in said melt-stable polymer composition;
   (i) said first polymer component being formed from at least:
      (A) a source of (R)-lactic acid residuals; and,
      (B) a source of (S)-lactic acid residuals;
   (ii) said first polymer component having (R)-lactic acid residuals and (S)-lactic acid residuals in a distribution in the polymer such that sequences of a major lactic acid residual have at least a 0.5 probability of including a sequence of less than 10 of the major lactic acid residuals consecutively;
(b) said first polymer component having a number average molecular weight of at least 40,000 and no greater than about 300,000; and,
(c) said melt stable polymer composition having a lactide concentration, if present at all, of less than about 2% by weight of melt-stable polymer in said first polymer component;
(d) said melt-stable first polymer component being a material in a form sufficiently melt stable such that a devolatilized sample of it, when isolated and prior to formation of said melt-stable polymer composition, will show formation of less than 1% lactide presence, by weight, after heating for 1 hour at 180° C.

* * * * *

UNITED STATES PATENT AND TRADEMARK OFFICE
CERTIFICATE OF CORRECTION

PATENT NO. : 5,585,191
DATED : Dec. 17, 1996
INVENTOR(S) : GRUBER ET AL.

It is certified that error appears in the above-indentified patent and that said Letters Patent is hereby corrected as shown below:

In column 1, line 67, "Use" should read --use--.

In column 3, the reaction

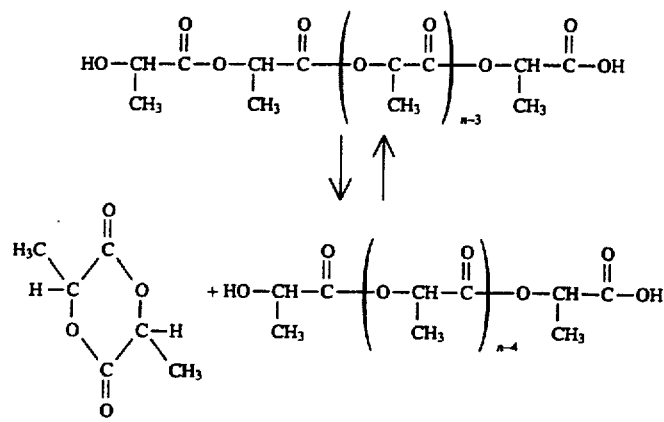

should read:

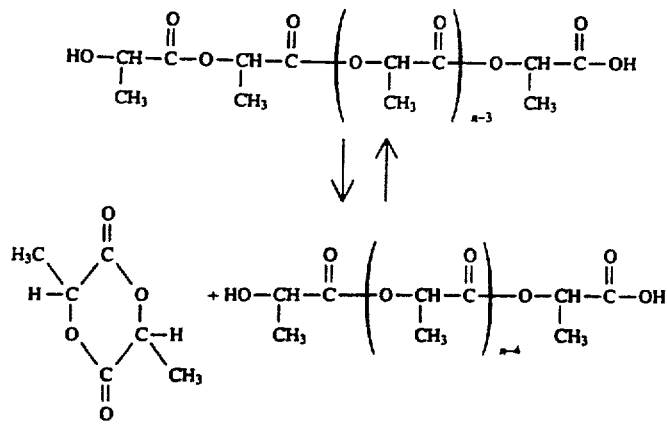

UNITED STATES PATENT AND TRADEMARK OFFICE
CERTIFICATE OF CORRECTION

PATENT NO. : 5,585,191

DATED : Dec. 17, 1996

INVENTOR(S) : GRUBER ET AL.

It is certified that error appears in the above-identified patent and that said Letters Patent is hereby corrected as shown below:

In column 6, line 34, insert --down to about 35 dynes/cm-- after the word "energy".

In column 11, lines 34 and 35, "Tg" should read --$T_g$--.

In column 19, line 32, "Tg" should read --$T_g$--.

In column 11, line 44, "27 and 27" should read --27 and 28--.

In column 29, line 45, "9" should read --15--.

In column 39, line 12, "teste" should read --test--.

In column 39, line 56, "pars" should read --parts--.

In column 41 (Table 29), line 15, "231,200" should read --231,300--.

Signed and Sealed this

Nineteenth Day of August, 1997

*Attest:*

BRUCE LEHMAN

*Attesting Officer*   *Commissioner of Patents and Trademarks*